US011684698B2

United States Patent
Takahashi et al.

(10) Patent No.: US 11,684,698 B2
(45) Date of Patent: Jun. 27, 2023

(54) CELL AGGREGATE INCLUDING RETINAL TISSUE AND PRODUCTION METHOD THEREFOR

(71) Applicants: Riken, Saitama (JP); Sumitomo Pharma Co., Ltd., Osaka (JP)

(72) Inventors: Masayo Takahashi, Wako (JP); Michiko Mandai, Wako (JP); Suguru Yamasaki, Kobe (JP)

(73) Assignees: Riken, Saitama (JP); Sumitomo Pharma Co., Ltd., Osaka (JP)

( * ) Notice: Subject to any disclaimer, the term of this patent is extended or adjusted under 35 U.S.C. 154(b) by 425 days.

(21) Appl. No.: 16/643,710

(22) PCT Filed: Sep. 7, 2018

(86) PCT No.: PCT/JP2018/033299
§ 371 (c)(1),
(2) Date: Mar. 2, 2020

(87) PCT Pub. No.: WO2019/050015
PCT Pub. Date: Mar. 14, 2019

(65) Prior Publication Data
US 2020/0206387 A1    Jul. 2, 2020

(30) Foreign Application Priority Data

Sep. 8, 2017 (JP) .............................. JP2017-173404

(51) Int. Cl.
| *A61K 35/30* | (2015.01) |
| *C12N 5/00* | (2006.01) |
| *C12N 5/071* | (2010.01) |
| *G01N 33/50* | (2006.01) |
| *A61L 27/38* | (2006.01) |
| *A61P 27/02* | (2006.01) |
| *A61L 27/40* | (2006.01) |

(52) U.S. Cl.
CPC .............. *A61L 27/38* (2013.01); *A61K 35/30* (2013.01); *A61L 27/40* (2013.01); *A61P 27/02* (2018.01); *C12N 5/0062* (2013.01); *C12N 5/0697* (2013.01); *G01N 33/5014* (2013.01); *G01N 33/5082* (2013.01); *C12N 2513/00* (2013.01); *C12N 2533/90* (2013.01)

(58) Field of Classification Search
None
See application file for complete search history.

(56) References Cited

FOREIGN PATENT DOCUMENTS

| JP | 2013-502234 A | 1/2013 |
| JP | 2013-128476 A | 7/2013 |
| WO | 2011/028524 A1 | 8/2010 |
| WO | 2012/173207 A1 | 12/2012 |
| WO | 2013/183774 A1 | 12/2013 |
| WO | 2015/025967 A1 | 2/2015 |
| WO | 2016/063985 A1 | 4/2016 |
| WO | 2016/063986 A1 | 4/2016 |
| WO | 2019/217630 A1 | 11/2019 |

OTHER PUBLICATIONS

Völkner et al. "Retinal organoids from pluripotent stem cells efficiently recapitulate retinogenesis." Stem Cell Reports 6.4 (2016): 525-538. (Year: 2016).*
Zhong et al. "Generation of three-dimensional retinal tissue with functional photoreceptors from human iPSCs." Nature Communications 5.1 (2014): 1-14. (Year: 2014).*
Mellough et al. "Lab generated retina: Realizing the dream." Visual Neuroscience 31.4-5 (2014): 317-332. (Year: 2014).*
Felemban et al. "Extracellular matrix component expression in hPSC-derived retinal organoids recapitulates retinogenesis in vivo and reveals an important role for IMPG1 and CD44 in the development of photoreceptors and interphotoreceptor matrix." Acta Biomaterialia 74 (2018): 207 (Year: 2018).*
Extended European Search Report issued in counterpart European Patent Application No. 18853297.2 dated Apr. 19, 2021.
Nakano et al., "Self-Formation of Optic Cups and Storable Stratified Neural Retina from Human ESCs", Cell Stem Cell, 10 (6), 1-18 Supplemental Information (2012).
Nakano et al., "Supplemental 1-3,6, Information Self-Formation of Optic Cups and Storable Stratified Neural Retina from Human ESCs," Cell Stem Cell, 10: 771-785 (2012).
Strauss, "The Retinal Pigment Epithelium in Visual Function," Physiological Reviews, 85 (3): 845-881 (2005).
Radtke et al., "Transplantation of intact sheets of fetal neural retina with its retinal pigment epithelium in retinitis pigmentosa patients," American Journal of Ophthalmology, 133 (4): 544-550 (2002).
International Search Report issued in corresponding International Patent Application No. PCT/JP2018/033299 dated Nov. 6, 2018.
International Preliminary Report on Patentability and Written Opinion issued in corresponding International Patent Application No. PCT/JP2018/033299 dated Mar. 19, 2020.
Seiler et al., "Co-transplantation of embryonic retina and retinal pigment epithelial cells to rabbit retina," Current Eye Research, 14: 199-207 (1995).
Kuwahara et al., "Generation of a ciliary margin-like stem cell niche from self-organizing human retinal tissue," Nature Communications, 6: 6286 (2015).
Wang et al., "New medium used in the differentiation of human pluripotent stem cells to retina cells is comparable to fetal human eye tissue," Biomaterials, 53: 40-49 (2015).

* cited by examiner

*Primary Examiner* — Emily A Cordas
(74) *Attorney, Agent, or Firm* — Morgan, Lewis & Bockius LLP

(57) ABSTRACT

A sphere-like cell aggregate according to one embodiment of the present invention comprises: a core part containing neural retina; and a covering part continuously or discontinuously covering at least a portion of a surface of the core part.

20 Claims, 10 Drawing Sheets

CELL AGGREGATE INCLUDING RETINAL TISSUE AND PRODUCTION METHOD THEREFOR

TECHNICAL FIELD

The present invention relates to a sphere-like cell aggregate containing neural retina and a method for producing the same. In particular, the present invention relates to a sphere-like cell aggregate comprising a core part containing neural retina and a covering part continuously or discontinuously covering at least a portion of the surface of the core part and containing retinal pigment epithelial cells, and a method for producing the same.

BACKGROUND ART

In instances where photoreceptor cells and retinal pigment epithelial (RPE) cells are simultaneously impaired, such as advanced age-related macular degeneration, simultaneous transplantation of neural retina (NR) and retinal pigment epithelial (RPE) cells is considered desirable.

In connection with retinal transplantation therapy for diseases based on retinal tissue disorders such as retinal pigment degeneration, researches on methods for producing neural retina and retinal pigment epithelial (RPE) cells from pluripotent stem cells have been actively conducted. As a method for producing neural retina from pluripotent stem cells, for example, a method for obtaining neural retina by subjecting an aggregate of pluripotent stem cells to suspension culture in a culture medium containing a BMP signaling pathway agonist is known (Patent Literatures 1 and 2 and Non Patent Literature 1). Furthermore, as a method for producing RPE cells from pluripotent stem cells, a method for obtaining RPE cells from retinal progenitor cells induced, for example, in a culture medium containing a retinoic acid receptor antagonist is known (Patent Literature 3). However, a method for producing a retinal tissue containing both NR and RPE cells in a state where both NR and RPE cells are correctly localized in a directional manner as in a retinal tissue in vivo is not known.

Until now, transplantation of a cell mixture of retinal progenitor cells and RPE cells (Non Patent Literature 2) and transplantation of RPE cell-retinal progenitor cell adhesion complex in which retinal progenitor cells are adhered to an RPE cell sheet (Patent Literature 4) have been reported.

However, in the cell mixture used in Non Patent Literature 2, cells are not adhered to each other, and the retinal progenitor cells adhered to the RPE cell sheet in Patent Literature 1 are not closely adhered to each other, thus they are not in a state capable of functioning as a retinal tissue. Thus, in either case, long-term engraftment after transplantation is expected to be poor.

CITATION LIST

Patent Literature

Patent Literature 1: WO 2015/025967
Patent Literature 2: WO 2016/063986
Patent Literature 3: WO 2012/173207
Patent Literature 4: U.S. Patent Application Publication No. 2016/0331867

Non Patent Literature

Non Patent Literature 1: Atsushi Kuwahara et al., Nature Communications, 6, 6286 (2015)

Non Patent Literature 2: Seiler et al., Curr Eye Res. 1995 March; 14(3): 199-207

SUMMARY OF INVENTION

Technical Problem

An object of the present invention is to provide a cell aggregate suitable for transplantation, containing a retinal tissue, in particular neural retina and retinal pigment epithelial cells, and a method for producing the same.

Solution to Problem

The present inventors have found that, by contacting RPE cells with a sphere-like cell aggregate containing neural retina, the sphere-like cell aggregate according to the present invention in which RPE cells are adhered to the cell aggregate can be obtained, and that good engraftment is observed when a cell sheet which is physically cut out from the aggregate is transplanted into a retinal degeneration nude rat, and have finally completed the present invention.

That is, the present invention relates to the following.

[1] A sphere-like cell aggregate comprising:
a core part containing neural retina; and
a covering part continuously or discontinuously covering at least a portion of a surface of the core part, wherein
(1) in the neural retina, a neural retinal layer including at least a photoreceptor layer is formed, wherein the photoreceptor layer contains one or more types of cells selected from the group consisting of at least a photoreceptor cell, a photoreceptor progenitor cell, and a retinal progenitor cell, and the cells contained in the photoreceptor layer are continuously present in a tangential direction to the surface of the core part;
(2) the covering part contains retinal pigment epithelial cells in contact with each other;
(3) the cell aggregate is free of a crystalline lens, a vitreous, a cornea, and a blood vessel; and
(4) the retinal pigment epithelial cells do not constitute an epithelial structure continued with the neural retinal layer.
[2] The sphere-like cell aggregate according to [1], wherein an extracellular matrix is present between the photoreceptor layer in (2) and the retinal pigment epithelial cells covering at least a portion of the photoreceptor layer.
[3] The sphere-like cell aggregate according to [2], wherein the extracellular matrix includes one or more extracellular matrices selected from the group consisting of hyaluronic acid, laminin, type IV collagen, heparan sulfate proteoglycan, and entactin.
[4] A method for producing the sphere-like cell aggregate according to any one of [1] to [3], comprising:
preparing a sphere-like cell aggregate containing neural retina (a cell aggregate of neural retina), wherein
(I) in the cell aggregate of neural retina, the neural retina is present on a surface of the cell aggregate; and
(II) in the neural retina, a neural retinal layer including at least a photoreceptor layer is formed, wherein in the photoreceptor layer, one or more types of cells selected from the group consisting of a retinal progenitor cell, a photoreceptor progenitor cell, and a photoreceptor cell are present;
preparing a retinal pigment epithelial cell; and
contacting the cell aggregate of neural retina with the retinal pigment epithelial cell.
[5] The production method according to [4], wherein in the cell aggregate of neural retina, a proportion of Chx10 positive cells present in the neural retina is 20% or more.

[6] The production method according to [4] or [5], wherein the contacting step is performed in the presence of an adhesion factor.

[7] The production method according to [6], wherein the adhesion factor is an extracellular matrix.

[8] The production method according to [7], wherein the extracellular matrix includes one or more extracellular matrices selected from the group consisting of hyaluronic acid, laminin, type IV collagen, heparan sulfate proteoglycan, and entactin.

[9] The production method according to any one of [4] to [7], wherein at least one of the cell aggregate of neural retina and the retinal pigment epithelial cell is derived from a pluripotent stem cell.

[10] The production method according to any one of [4] to [8], wherein in the step of preparing the retinal pigment epithelial cell, the retinal pigment epithelial cell is prepared as a cell sheet or a cell suspension.

[11] The production method according to any one of [4] to [10], wherein after the contacting step, further culture is performed until the retinal pigment epithelial cell has a polygonal or flagstone-like cell morphology.

[12] A reagent for evaluating toxicity or drug efficacy of a test substance, comprising the sphere-like cell aggregate according to any one of [1] to [3].

[13] A method for evaluating toxicity or drug efficacy of a test substance, comprising:
  contacting the sphere-like cell aggregate according to any one of [1] to [3] or a portion of the sphere-like cell aggregate with the test substance; and
  examining an effect of the test substance on the sphere-like cell aggregate or a cell contained in the sphere-like cell aggregate.

[14] A drug for treating a disease based on a disorder of a retinal pigment epithelial cell, a retinal cell or a retinal tissue or a damage of a retinal tissue, comprising the sphere-like cell aggregate according to any one of [1] to [3] or a portion of the sphere-like cell aggregate.

[15] A method for treating a disease based on a disorder of a retinal pigment epithelial cell, a retinal cell or a retinal tissue or a damage of a retinal tissue, comprising transplanting an effective amount of the sphere-like cell aggregate according to any one of [1] to [3] or a portion of the sphere-like cell aggregate into a subject in need of transplantation.

[16] The sphere-like cell aggregate according to any one of [1] to [3] or a portion of the sphere-like cell aggregate, for use in treatment of a disease based on a disorder of a retinal pigment epithelial cell, a retinal cell or a retinal tissue or a damage of a retinal tissue.

[17] A pharmaceutical composition comprising the sphere-like cell aggregate according to any one of [1] to [3] or a portion of the sphere-like cell aggregate as an active ingredient.

[18] A portion of the sphere-like cell aggregate according to any one of [1] to [3], wherein the portion is physically cut out from the sphere-like cell aggregate.

[19] A portion of the sphere-like cell aggregate according to [18], wherein the portion is in the form of a cell sheet containing a retinal pigment epithelial cell and neural retina.

[20] A method for producing a portion of a sphere-like cell aggregate, comprising a step of physically cutting out the portion of the sphere-like cell aggregate according to any one of [1] to [3].

[21] The production method according to [20], wherein the portion of the sphere-like cell aggregate is in the form of a cell sheet containing a retinal pigment epithelial cell and neural retina.

Advantageous Effects of Invention

According to the present invention, a cell aggregate suitable for transplantation, containing a retinal tissue, in particular neural retina and retinal pigment epithelial cells, which enable each retinal cell to engraft over a long period of time at appropriate locations to be present in vivo, and a method for producing the same can be provided.

DESCRIPTION OF EMBODIMENTS

[Sphere-Like Cell Aggregate]

Figure 1:
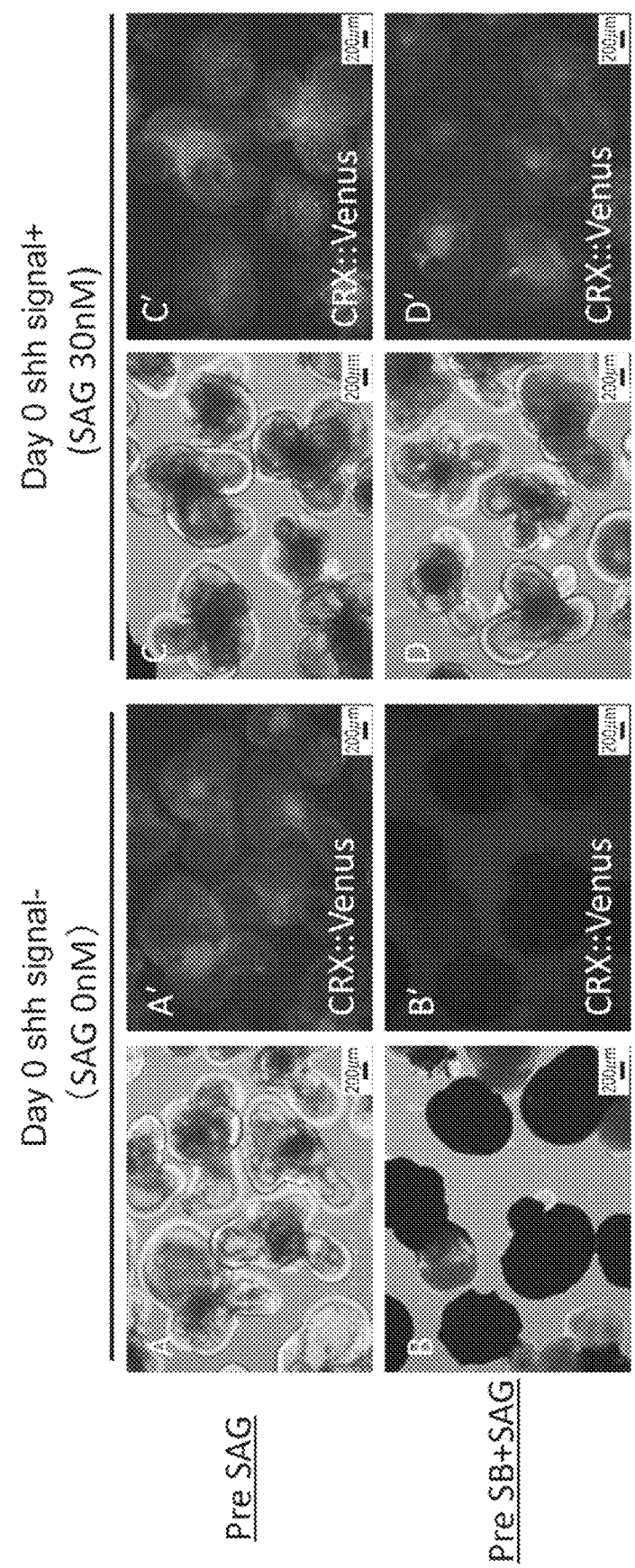
FIG. 1 is diagrams showing microscopic observation results (A, B, C, D) and fluorescence microscopic observation results (A', B', C', D') of separately prepared retinal pigment epithelial (RPE) cells and neural retina (NR) which were differentiated from human ES cells.

A sphere-like cell aggregate according to one embodiment of the present invention comprises a core part containing neural retina and a covering part continuously or discontinuously covering at least a portion of the surface of the core part, and has the following features (1) to (4):

(1) in the neural retina, a neural retinal layer including at least a photoreceptor layer is formed, wherein the photoreceptor layer contains one or more types of cells selected from the group consisting of at least a photoreceptor cell, a photoreceptor progenitor cell, and a retinal progenitor cell, and the cells contained in the photoreceptor layer are continuously present in a tangential direction to the surface of the core part;

(2) the covering part includes retinal pigment epithelial cells in contact with each other;

(3) the cell aggregate is free of a crystalline lens, a vitreous, a cornea, and a blood vessel; and (4) the retinal pigment epithelial cells do not constitute an epithelial structure continued with the neural retinal layer.

The "sphere-like cell aggregate" means a cell aggregate having a stereoscopic shape close to globular. Examples of the stereoscopic shape close to globular include a globular shape which is a shape having a three-dimensional structure and indicating, when projected onto a two-dimensional surface, for example, a circle or an ellipse, and a shape formed by fusing a plurality of globular shapes (indicating, for example, when projected onto a two-dimensional surface, a shape formed by overlapping two to four circles or ellipses). In one embodiment, the core part of the aggregate has a vesicular layered structure, and has a feature that, under a bright field microscope, the central portion thereof is observed darker and the outer edge portion thereof is observed brighter.

The "cell aggregate" is not particularly limited as long as a plurality of cells adhere to each other to form a steric structure. For example, the cell aggregate refers to a mass formed by aggregation of cells dispersed in a medium such as a culture medium, or a cell mass formed through cell division. The cell aggregate also includes a cell aggregate which forms a specific tissue.

The core part of the cell aggregate includes neural retina. The "retinal tissue" or "retinal organoid" means a tissue in which one or more types of retinal cells constituting each retinal layer in a retina in vivo are contained in a layered manner and sterically. The "neural retina" means a retinal tissue that does not include a retinal pigment epithelial layer but includes a neural retinal layer present inside the retinal pigment epithelial layer among retinal layers described later. Whether each cell is a cell constituting any of retinal layers can be confirmed by a known method, for example, the presence or absence of expression of a cell marker or the degree of expression.

Some regions of the "core part of cell aggregate" may include retinal pigment epithelial cells and/or a ciliary marginal zone-like structure. In one embodiment, a portion of the continuous boundary surface (constituted by neural retina) formed against the external environment of the cell aggregate is constituted by retinal pigment epithelial cells, and a ciliary marginal zone-like structure is present in the boundary region between the neural retina and the retinal pigment epithelial cells. Specific examples of such a "core part of cell aggregate" include a cell aggregate disclosed in WO 2013/183774 (FIG. 12A).

The "retinal cell" means a cell constituting each retinal layer in a retina in vivo or a progenitor cell thereof. Specific examples of the retinal cells include, but are not limited to, photoreceptor cells (rod photoreceptor cells, cone photoreceptor cells), horizontal cells, amacrine cells, interneuron cells, retinal ganglion cells (ganglion cells), bipolar cells (rod bipolar cells, cone bipolar cells), Müller glial cells, retinal pigment epithelial (RPE) cells, ciliary marginal zone cells, progenitor cells of these (e.g., photoreceptor progenitor cells, bipolar progenitor cells), and retinal progenitor cells. Among the above retinal cells, specific examples of the cells constituting a neural retinal layer include photoreceptor cells (rod photoreceptor cells, cone photoreceptor cells), horizontal cells, amacrine cells, interneuron cells, retinal ganglion cells (ganglion cells), bipolar cells (rod bipolar cells, cone bipolar cells), Müller glial cells, and progenitor cells of these (e.g., photoreceptor progenitor cells, bipolar progenitor cells).

The "mature retinal cell" means a cell that may be contained in the retinal tissue of a human adult. Specific examples of the mature retinal cell include differentiated cells such as photoreceptor cells (rod photoreceptor cells, cone bipolar cells), horizontal cells, amacrine cells, intervening nerve cells, retinal ganglion cells (ganglion cells), bipolar cells (rod bipolar cells, cone bipolar cells), Müller glial cells, retinal pigment epithelial (RPE) cells, and ciliary marginal zone cells. The "immature retinal cell" means a progenitor cell that has been determined to differentiate into a mature retinal cell. Examples of the immature retinal cell include photoreceptor progenitor cells, bipolar progenitor cells, or retinal progenitor cells.

The photoreceptor progenitor cell, horizontal progenitor cell, bipolar progenitor cell, amacrine progenitor cell, retinal ganglion progenitor cell, Müller glial progenitor cell, and retinal pigment epithelial progenitor cell means a progenitor cell that has been determined to differentiate into a photoreceptor cell, horizontal cell, bipolar cell, amacrine cell, retinal ganglion cell, Müller glial cell, and retinal pigment epithelial cell, respectively.

The "retinal progenitor cell" refers to a progenitor cell that can differentiate into any of immature retinal cells, such as a photoreceptor progenitor cell, horizontal progenitor cell, bipolar progenitor cell, amacrine progenitor cell, retinal ganglion progenitor cell, Müller glial progenitor cell, and retinal pigment epithelial progenitor cell, and can ultimately differentiate into any of mature retinal cells, such as a photoreceptor cell, rod photoreceptor cell, cone bipolar cell, horizontal cell, bipolar cell, amacrine cell, retinal ganglion cell, and retinal pigment epithelial cell.

The "photoreceptor cell" is present in the photoreceptor layer of retina and has a role of absorbing a light stimulus and converting it into an electrical signal. There are two types of photoreceptor cells, a cone that functions in the light place and a rod that functions in the dark place. Photoreceptor cells are differentiated from photoreceptor progenitor cells to mature. Whether a cell is a photoreceptor cell or a photoreceptor progenitor cell can be easily confirmed by those skilled in the art by, for example, expression of cell markers (such as Crx and Blimp1 expressed in photoreceptor progenitor cells; recoverin expressed in photoreceptor cells; and rhodopsin, S-Opsin, M/L-Opsin expressed in mature photoreceptor cells) described below, and formation of outer segment structure. In one embodiment, the photoreceptor progenitor cells are Crx positive cells and the photoreceptor cells are rhodopsin, S-Opsin and M/L-Opsin positive cells.

The "retinal pigment epithelial cell" means an epithelial cell present outside neural retina in retina in vivo. Whether a cell is a retinal pigment epithelial cell or not can be easily confirmed by those skilled in the art by, for example, expression of cell markers (such as RPE65, Mitf, CRALBP, MERTK, BEST1, etc.) described below, presence of melanin granules (melanin brown), tight junction between cells, and characteristic polygonal or cobblestone-like cell morphology. Whether a cell has the function of retinal pigment epithelial cell or not can be easily confirmed by, for example, the secretory capacity of cytokines such as VEGF and PEDF. In one embodiment, retinal pigment epithelial cells are RPE65 positive cells, Mitf positive cells, or RPE65 positive and Mitf positive cells.

The presence of retinal cells can be confirmed by the presence or absence of expression of a marker for retinal cells (hereinafter sometimes referred to as "retinal cell marker"). The presence or absence of expression of retinal cell markers, or proportion of retinal cell marker positive cells in a cell population or tissue can be easily confirmed by those skilled in the art. For example, it can be confirmed by dividing the number of specific retinal cell marker positive cells by the total number of cells using a technique such as flow cytometry or immunostaining with commercially available antibodies.

Examples of the retinal cell marker include Rx (also referred to as "Rax"), PAX6 and Chx10 expressed in retinal progenitor cells; Crx and Blimp 1 expressed in photoreceptor progenitor cells; recoverin expressed in photoreceptor cells; Chx10, PKCα and L7 expressed in bipolar cells; TuJ1 and Brn3 expressed in retinal ganglion cells; calretinin expressed in amacrine cells; calbindin expressed in horizontal cells; rhodopsin expressed in mature photoreceptor cells; Nrl and rhodopsin expressed in rod photoreceptor cells; Rxr-γ, S-Opsin and M/L-Opsin expressed in cone photoreceptor cells; GS and GFAP expressed in Müller glial cells; RPE65 and Mitf expressed in retinal pigment epithelial cells; and Rdh10 and SSEA1 expressed in ciliary marginal zone cells.

The "positive cell" means a cell expressing a specific marker on the cell surface or in the cell. For example, the "Chx10 positive cell" means a cell expressing Chx10 protein in the nucleus.

(1) In the neural retina of the core part of the sphere-like cell aggregate, neural retinal layers including at least a photoreceptor layer is formed. The "retinal layer" means each layer constituting the retina. Specific examples of the retinal layer include a retinal pigment epithelial layer, a photoreceptor layer, an outer limiting membrane, an outer nuclear layer, an outer plexiform layer, an inner nuclear layer, an inner plexiform layer, a ganglion cell layer, a nerve fiber layer and an inner limiting membrane. The "neural retinal layer" means each layer constituting neural retina. Specific examples of the neural retinal layer include a photoreceptor layer, an outer limiting membrane, an outer nuclear layer, an outer plexiform layer, an inner nuclear layer, an inner plexiform layer, a ganglion cell layer, a nerve fiber layer, and an inner limiting membrane. The "photoreceptor layer" means a retinal layer that is a kind of retinal layer or neural retinal layer, formed outermost of neural retina, and contains a large number of photoreceptor cells (rod photoreceptor cells, cone photoreceptor cells), photoreceptor progenitor cells, and retinal progenitor cells.

The photoreceptor layer in the neural retina of the core part contains one or more types of cells selected from the group consisting of at least a photoreceptor cell, a photoreceptor progenitor cell, and a retinal progenitor cell (hereinafter sometimes referred to as "photoreceptor cell and the like"), where the photoreceptor cell includes rod and cone photoreceptor cells, and the photoreceptor cell and the like comprise 70% or more, preferably 80% or more, more preferably 90% or more of the total cells present in the photoreceptor layer based on the number of nuclei. The photoreceptor layer in the neural retina of the core part is formed at least outermost of the core part of the aggregate and may also be formed inside of that. The photoreceptor cell and the like are present in a tangential direction to the surface of the core part continuously, i.e., adhered to each other, and form a photoreceptor layer containing the photoreceptor cell and the like by being present in a tangential direction to the surface of the core part continuously. The tangential direction refers to a tangential direction with respect to the surface of the core part (neural retina) of the sphere-like cell aggregate, i.e., a direction in which photoreceptor cell and the like form a line in the photoreceptor layer, and a direction which is parallel or transverse to the neural retina.

One embodiment of the neural retina of the core part may also be a so-called turnip-shaped aggregate (Non Patent Literature 1) that further contains a mass of retinal pigment epithelial cells in the same aggregate and has a ciliary marginal zone-like structure in the boundary region between the neural retina and retinal pigment epithelial cells described above.

The ciliary marginal zone-like structure is a structure similar to ciliary marginal zone. Examples of the "ciliary marginal zone (CMZ)" include a tissue present in a boundary region between neural retina and retinal pigment epithelial in a retina in vivo, in which the tissue is a region including tissue stem cells of retina (retinal stem cells). The ciliary marginal zone is also referred to as a ciliary margin or retinal margin, and the ciliary marginal zone, ciliary margin and retinal margin are equivalent tissues. It is known that the ciliary marginal zone plays an important role in supplying retinal progenitor cells and differentiated cells to retinal tissues, maintaining the retinal tissue structure, and the like. Examples of marker genes for the ciliary marginal zone include Rdh10 gene (positive), Otx1 gene (positive), and ZiC1 (positive).

(2) The covering part of the sphere-like cell aggregate covers continuously or discontinuously at least a portion of the surface of the core part of the cell aggregate. Here, the surface of the core part of the sphere-like cell aggregate means a surface of the outermost photoreceptor layer present on the surface of neural retina of the core part. The covering part preferably covers 30% or more, more preferably 50% or more, of the surface area of the core part. Covering continuously the surface of the core part means that the covering part is present as one continuous mass on the surface of the core part. Covering discontinuously the surface of the core part means that the covering part is present as two or more continuous masses or layers on the surface of the core part and each continuous mass is not connected to each other. In the case where the covering part discontinuously covers the surface of the core part, it is preferable that each continuous mass continuously covers 10% or more, or 20% or more of the surface area of the core part.

The covering part contains retinal pigment epithelial (RPE) cells in contact with each other, where the RPE cells include retinal pigment epithelial progenitor cells. The RPE cells "in contact with each other" means a state in which one RPE cell is in contact with another RPE cell in the covering part, and an independent single RPE cell that is not in contact with another RPE cell does not constitute the covering part.

One or more extracellular matrices may further be present as a portion of the covering part between the photoreceptor layer present on the surface of the core part and the retinal pigment epithelial cells covering at least a portion of the photoreceptor layer. The extracellular matrix means a biopolymer that constitutes the space outside of the cell. Examples of the extracellular matrix include cell adhesion proteins such as fibronectin, vitronectin and laminin, fibrous proteins such as collagen and elastin, fragments of these proteins, and glucosaminoglycan or proteoglycan such as hyaluronic acid and chondroitin sulfate. Preferably, the extracellular matrix includes one or more extracellular matrices selected from the group consisting of hyaluronic acid, laminin, type IV collagen, heparan sulfate proteoglycan and entactin. Examples of suitable extracellular matrix include fragments of laminin (e.g., laminin 511-E8 fragment, laminin 521-E8 fragment).

(3) While a retina in vivo including fetal retina contains a crystalline lens, a vitreous, a cornea, and a blood vessel, the sphere-like cell aggregate according to the present invention does not contain a crystalline lens, a vitreous, a cornea, and a blood vessel.

The "crystalline lens" is a tissue that acts as a lens reflecting light that enters the eyeball from the outside and focusing on retina. Examples of the partial structure of the crystalline lens include crystalline lens epithelium, crystalline lens nucleus, and crystalline lens sac. Examples of progenitor tissues of crystalline lens include crystalline lens placodes and crystalline lens vesicles. The crystalline lens placode is a crystalline lens progenitor tissue consists of a thickened epidermal ectoderm cell layer. In embryogenesis, the crystalline lens placode is formed by contact of Optic vesicle with epidermal ectoderm which leads to thickening of the contact region. The crystalline lens vesicle is a vesicle formed by intrusion of the crystalline lens placode. The presence of the crystalline lens, its partial structure, or its progenitor tissue can be confirmed by expression of a marker. Examples of the marker for crystalline lens, its partial structure, or its progenitor tissue marker include, but are not limited to, L-Maf (crystalline lens progenitor tissue), α, β and γ crystallin (crystalline lens).

The "vitreous" is a transparent jelly-like tissue that is behind the crystalline lens and fills the lumen and has the action of maintaining the shape of eyeball while dispersing the external force. The vitreous is made of moisture and protein (collagen). The presence of the vitreous can be confirmed by its jelly-like form.

The "cornea" is a transparent, watch glass-like tissue that occupies anterior about one sixth of the outer layer of ocular wall. Examples of partial structures of the cornea include corneal epithelium, bowman's membrane, corneal stroma, Descemet's membrane, and corneal endothelium. The cornea is typically constituted by five layers consisting of corneal epithelium, Bowman's membrane, corneal stroma, Descemet's membrane, and corneal endothelium in order from the body surface side. The presence of the cornea, its partial structure, or its progenitor tissue can be confirmed by expression of a marker. Examples of the marker for the cornea, its partial structure, or its progenitor tissue include pan-cytokeratin (corneal epithelial progenitor tissue), E-cadherin (corneal epithelial progenitor tissue), cytokeratin 3 (corneal epithelium), cytokeratin 12 (corneal epithelium), cytokeratin 14 (corneal epithelium), p63 (corneal epithelium), ZO-1 (corneal epithelium), PDGFR-α (corneal stroma, corneal endothelium, or progenitor tissues of these), Pitx2 (progenitor tissues of corneal stroma and corneal endothelium), and ABCG2 (progenitor tissues of corneal stroma and corneal endothelium).

When crystalline lens or the like is removed from fetal retina, holes are opened in that part and tissue is divided by voids. In addition, the number of cells that exist in inner layers constituting the neural retinal layer of the core part (the part excluding the outermost photoreceptor layer) of the sphere-like cell aggregate (e.g., horizontal cells, amacrine cells, bipolar cells) and ganglion cells is small compared to that in a retina in vivo. Specifically, it is, for example, 80% or less, 70% or less, 60% or less, or 50% or less compared to the number of cells present in inner layers of human fetal retina. In addition, when a portion of the fetal retina is cut out and cultured, it becomes a sheet structure having a two-dimensional thickness, but cannot become a three-dimensional sphere-like cell aggregate.

On the other hand, Optic cup that is artificially manufactured by differentiating pluripotent stem cells is known (e.g., Nature. 2011 Apr. 7; 472 (7341): 51-6), but the Optic cup has a hole in a portion of the cell aggregate and the tissue is divided by voids.

(4) Retinal pigment epithelial cells in the covering part do not constitute an epithelial structure continued with the neural retinal layer. The "epithelial structure" means the layer structure formed by an epithelial tissue, and a continuous epithelial structure means that the epithelial structure is formed from one continuous epithelial tissue. That is, the retinal pigment epithelial cells in the covering part and the neural retinal layer constituting neural retina in the core part in the sphere-like cell aggregate do not have continuity as an epithelial tissue. Whether an epithelial structure is continued or not can be confirmed by those skilled in the art by observing the state of tissue and the state of cell arrangement under a microscope.

A retina in vivo has an epithelial structure in which two roughly internal and external epithelial tissues overlap, where the internal side consists of neural retina and the external side consists of retinal pigment epithelial cells. This epithelial structure is formed by folding one continuous epithelial tissue. As a specific example, fetal retina is an epithelium in which neural retina-ciliary body-RPE are continuous as a single epithelial sheet. Artificially manufactured Optic cup also has a structure in which neural retina and RPE are continuous as a single epithelial sheet.

In one embodiment, the sphere-like cell aggregate according to the present invention includes a mammalian cell. The sphere-like cell aggregate according to the present invention preferably contains a rodent (e.g., mouse, rat) or primate (e.g., human, monkey) cells, more preferably contains a human cell.

In one embodiment, the sphere-like cell aggregate according to the present invention is a sphere-like cell aggregate for use in treatment of a disease based on a disorder of a retinal pigment epithelial cell, a retinal cell or a retinal tissue or a damage of a retinal tissue (especially, a severe case in which a photoreceptor cell and a retinal pigment epithelial cell are simultaneously impaired or damaged).

In one embodiment, the sphere-like cell aggregate according to the present invention can be transplanted into a subject in need of transplantation (e.g., a mammal), and the transplantation can improve visual function. Examples of the mammal to be a subject include human, mouse, rat, guinea pig, hamster, rabbit, cat, dog, sheep, pig, cow, horse, goat, and monkey.

Upon transplantation, the sphere-like cell aggregate may be stored in a medium necessary to maintain the viability of the sphere-like cell aggregate. Examples of the "medium necessary to maintain viability" include a culture medium and a physiological buffer solution, but are not particularly limited as long as a cell population containing retinal cells such as retinal progenitor cells is viable, and can be appropriately selected by those skilled in the art. Specific examples thereof include a culture medium prepared using a culture medium usually used for culturing animal cells as a basal medium. Examples of the basal medium include a medium that can be used for culturing animal cells, such as BME medium, BGJb medium, CMRL 1066 medium, Glasgow MEM (GMEM) medium, Improved MEM Zinc Option medium, Neurobasal™ medium, IMDM medium, Medium 199 medium, Eagle MEM medium, αMEM medium, DMEM medium, F-12 medium, DMEM/F12 medium, IMDM/F12 medium, ham medium, RPMI 1640 medium, Fischer's medium, or a mixed medium of these.

In one embodiment, the sphere-like cell aggregate according to the present invention can be transplanted after being sliced in an appropriate size using forceps, a knife, scissors, or the like. The shape after cutting out is not limited, but examples thereof include a sheet agent containing neural retina and retinal pigment epithelial cells (also referred to as a cell sheet or an NR-RPE cell sheet). For example, one cell sheet (for example, a diameter of 300 μm and a height of 50 μm) cut out from one cell aggregate is transplanted by one to a plurality of sheets depending on the area of the region where the photoreceptor cells and retinal pigment epithelial cells are degenerated. Those skilled in the art can select the number of cell sheets depending on the region where degenerative death has occurred.

The transplantation is performed, for example, by a method of transplanting sub-retinally using an injection needle, or by incising a portion of the eyeball and transplanting from the incision site to the damaged site or lesion site.

At least a portion of the immature retinal cells engrafted after transplantation are induced to differentiate into mature retinal cells under in vivo (intraocular) environment of the subject. Here, the "photoreceptor cells induced after transplantation" means photoreceptor cells induced to differentiate from retinal progenitor cells or photoreceptor progenitor cells engrafted after transplantation in the eye of the subject.

The "engraftment" as used herein means that the transplanted cells survive in the living body for a long period of time (e.g., 30 days or more, 60 days or more, 90 days or more) and adhered to remain in the organ.

The "contact ratio" as used herein refers to a ratio of the length of the photoreceptor layer of the transplanted retinal tissue contact with the retinal layer containing bipolar cells on the host side relative to the major axis of the transplanted retinal tissue.

The "functional engraftment" as used herein means a state in which transplanted cells have engrafted and performs their original functions in vivo.

The "functional engraftment ratio" as used herein means a proportion of the cells that have achieved functional engraftment among the transplanted cells. The functional engraftment ratio of the transplanted photoreceptor cells can be determined, for example, from the contact ratio described above.

The functional engraftment ratio of the photoreceptor cells (including photoreceptor cells induced after transplantation) transplanted by transplanting the above sphere-like cell aggregate is 10% or more, preferably 20% or more, more preferably 40% or more, further preferably 50% or more, still preferably 60% or more.

A retina in vivo has a very complex layer structure and functions only after the cells in the retinal layer are orderly present in a methodical manner. The sphere-like cell aggregate has a neural retinal layer including at least a photoreceptor layer, and in the retinal layer, photoreceptor cell and the like adhere to each other and are present continuously, and retinal pigment epithelial cells are present in the covering part. Thus, the sphere-like cell aggregate has a structure very similar to that of a retina in vivo. Thus, by transplanting the sphere-like cell aggregate according to the present invention, it is expected to be engrafted in a living body for a long period of time by exercising both photoreceptive function by the photoreceptor cells and photoreceptor cell-protective function or the like by the retinal pigment epithelial cells, as an alternative to retina and retinal pigment epithelial cells that have been impaired in the living body. Accordingly, the sphere-like cell aggregate is a cell aggregate suitable for transplantation. Moreover, the sphere-like cell aggregate according to the present invention can be produced by the production method described below, thus it can be said to be superior to a retina in vivo in that it is possible to provide a required amount in a timely manner to patients in need of transplantation.

[Production Method of Sphere-Like Cell Aggregate]

The method for producing a sphere-like cell aggregate according to one embodiment of the present invention includes the steps of preparing a sphere-like cell aggregate containing neural retina (a cell aggregate of neural retina), preparing a retinal pigment epithelial cell, and contacting the cell aggregate of neural retina with the retinal pigment epithelial cell.

(Cell Aggregate of Neural Retina)

Hereinafter, the cell aggregate of neural retina and methods for producing the same are described. The "cell aggregates of neural retina" means a sphere-like cell aggregate containing neural retina.

(I) In the sphere-like cell aggregate containing neural retina (a cell aggregate of neural retina), the neural retina is present on the surface of the cell aggregate. For example, the neural retina has a thickness on the surface of the cell aggregate of neural retina, forming a boundary of a continuous surface against the external environment. The boundary surface facing the external environment is occupied by a large number of photoreceptor cells, and inner layer cells and retinal progenitor cells are present inside of the boundary surface. The cells that constitute these retinal layers adhere to each other and are present continuously. Since cavities or spaces where orderly lined layers are not formed are present at the inside, a clear shadow is observed at the border, thus it is confirmed that an epithelial structure is formed. The sphere-like cell aggregate containing neural retina corresponds to the core part of the sphere-like cell aggregate comprising a core part and a covering part described above.

(II) In the neural retina, a neural retinal layer including at least a photoreceptor layer is formed, and in the photoreceptor layer, one or more types of cells selected from the group consisting of a photoreceptor cell, a photoreceptor progenitor cell, and a retinal progenitor cell are present. The proportion of Chx10 positive cells present in the neural retina is 20% or more, preferably 30% or more, and more preferably 40% or more. Examples of the Chx10-positive cell include retinal progenitor cells and photoreceptor progenitor cells.

It is preferred that the cell aggregate of neural retina is derived from a pluripotent stem cell. The "pluripotent stem cell" refers to a stem cell that can be cultured in vitro and has an ability to differentiate into all cells (tissues derived from three germ layers (ectoderm, mesoderm, endoderm)) that constitute a living organism other than placenta, that is, pluripotency. Embryonic stem cells are also included in pluripotent stem cells.

Pluripotent stem cells can be derived from fertilized eggs, cloned embryos, germline stem cells, tissue stem cells, somatic cells and the like. Examples of the pluripotent stem cells include embryonic stem cells (ES cells), embryonic germ cells (EG cells), and induced pluripotent stem cells (iPS cells). Multi-lineage differentiating stress enduring cells (Muse cells) obtained from mesenchymal stem cells (MSCs) and GS cells produced from germ cells (e.g., testis) are also included in pluripotent stem cells. Embryonic stem cells were first established in 1981 and have been applied to the production of knockout mice since 1989. In 1998, human embryonic stem cells were established and are being used in regenerative medicine. Embryonic stem cells can be produced by culturing an inner cell mass on a feeder cell or in a culture medium comprising a leukemia inhibitory factor (LIF). Methods for producing embryonic stem cells are described, for example, in WO 96/22362, WO 02/101057, U.S. Pat. Nos. 5,843,780, 6,200,806, and 6,280,718. Embryonic stem cells can be obtained from prescribed institutions or can be purchased commercially. For example, KhES-1, KhES-2 and KhES-3, which are human embryonic stem cells, are available from Institute for Frontier Medical Sciences, Kyoto University. Rx::GFP strain (derived from KhES-1 strain), which is a human embryonic stem cell, is available from RIKEN, National Research and Development Institute. EB5 and D3 cell lines, which are mouse embryonic stem cells, are available from RIKEN, National Research and Development Institute and ATCC, respectively.

Nuclear transfer embryonic stem cells (ntES cells), one of the embryonic stem cells, can be established from cloned embryo generated by transplanting nuclei of somatic cells into enucleated eggs.

EG cells can be produced by culturing primordial germ cells in a culture medium containing mSCF, LIF, and bFGF (Cell, 70: 841-847, 1992).

The "induced pluripotent stem cell" in the present invention is a cell in which pluripotency is induced by reprogramming a somatic cell by known methods and the like. Specific examples thereof include cells that are obtained by reprogramming fibroblasts or differentiated somatic cells such as peripheral blood mononuclear cells by expression of any combination of multiple genes selected from the reprogramming gene group including Oct3/4, Sox2, Klf4, Myc (c-Myc, N-Myc, L-Myc), Glis1, Nanog, Sall4, lin28, Esrrb or the like to induce pluripotency. Preferred examples of the combination of reprogramming factors include (1) Oct3/4, Sox2, Klf4, and Myc (c-Myc or L-Myc), and (2) Oct3/4, Sox2, Klf4, Lin28, and L-Myc (Stem Cells, 2013; 31: 458-466). Induced pluripotent stem cells were established by Yamanaka et al. from mouse cells in 2006 (Cell, 2006, 126(4), pp. 663-676). Induced pluripotent stem cells were also established from human fibroblasts in 2007, and have pluripotency and self-renewal ability similar to embryonic stem cells (Cell, 2007, 131(5), pp. 861-872; Science, 2007, 318 (5858), pp. 1917-1920; Nat. Biotechnol., 2008, 26(1), pp. 101-106).

In addition to the methods for producing directly induced pluripotent stem cells by reprogramming with gene expression, induced pluripotent stem cells can be induced from somatic cells by addition of compounds or the like (Science, 2013, 341, PP. 651-654).

It is also possible to obtain established induced pluripotent stem cells. For example, human induced pluripotent cell lines such as 201B7 cells, 201B7-Ff cells, 253G1 cells, 253G4 cells, 1201C1 cells, 1205D1 cells, 1210B2 cells, 1231A3 cells established at Kyoto University are available from Kyoto University. As established induced pluripotent stem cells, for example, Ff-I01 cells and Ff-I14 cells established at Kyoto University are available from Kyoto University.

The somatic cells used in producing induced pluripotent stem cells are not particularly limited, but examples thereof include fibroblasts derived from tissues, blood cell lines (e.g., peripheral blood mononuclear cells (PBMCs), T cells), hepatocytes, pancreatic cells, intestinal epithelial cells, and smooth muscle cells.

In the production of induced pluripotent stem cells, when reprogramming by expression of several types of genes, the means for expressing the genes are not particularly limited. Examples of the means include infection methods with viral vector (e.g., retrovirus vector, lentivirus vector, sendai virus vector, adenovirus vector, adeno-associated virus vector); gene transfer methods (e.g., calcium phosphate method, lipofection method, retronectin method, electroporation method) with plasmid vector (e.g., plasmid vector, episomal vector); gene transfer methods (e.g., calcium phosphate method, lipofection method, electroporation method) with RNA vector; and direct protein injection methods (for example, a method using a needle, lipofection method, electroporation method).

Induced pluripotent stem cells can be produced in the presence of feeder cells or in the absence of feeder cells (feeder-free). When producing induced pluripotent stem cells in the presence of feeder cells, the induced pluripotent stem cells can be produced by a known method in the presence of a factor for maintaining undifferentiated state. The culture medium used in the production of induced pluripotent stem cells in the absence of feeder cells is not particularly limited, but examples thereof include a known maintenance medium for embryonic stem cells and/or induced pluripotent stem cells, or a medium for establishing induced pluripotent stem cells at feeder-free. Examples of the medium for establishing induced pluripotent stem cells at feeder-free include feeder-free medium such as Essential 8™ medium (E8 medium), Essential 6™ medium, TeSR™ medium, mTeSR™ medium, mTeSR-E8™ medium, Stabilized Essential 8™ medium, and Stem Fit medium. Induced pluripotent stem cells can be produced, for example, by genetically transferring four factors Oct3/4, Sox2, Klf4, and Myc into a somatic cell using sendai virus vectors at feeder-free.

The pluripotent stem cells used in the present invention are preferably embryonic stem cells or induced pluripotent stem cells, more preferably, induced pluripotent stem cells.

The pluripotent stem cells used in the present invention are mammalian pluripotent stem cells, preferably rodent (e.g., mouse, rat) or primate (e.g., human, monkey) pluripotent stem cells, more preferably human or mouse pluripotent stem cells, and even more preferably human induced pluripotent stem cells (iPS cells) or human embryonic stem cells (ES cells).

Examples of multipotent stem cells include tissue stem cells (also referred to as histological stem cells, tissue-specific stem cells, or somatic stem cells) such as hematopoietic stem cells, neural stem cells, retinal stem cells, and mesenchymal stem cells.

The cell aggregates of neural retina can be obtained by inducing differentiation of pluripotent stem cells. Examples of the methods of the differentiation induction include, but are not limited to, the methods disclosed in WO 2011/055855, WO 2013/077425, WO 2015/025967, WO 2016/063985, WO 2016/063986, WO 2017/183732, PLoS One. 2010 Jan. 20; 5(1):e8763., Stem Cells. 2011 August; 29(8): 1206-18., Proc Natl Acad Sci USA. 2014 Jun. 10; 111(23): 8518-23, and Nat Commun. 2014 Jun. 10; 5: 4047.

As a specific embodiment, the cell aggregate of neural retina can be prepared by a method comprising the following steps (A), (B) and (C):

(A) a step of culturing a pluripotent stem cell in a culture medium containing 1) a TGFβ family signaling pathway inhibitor and/or a sonic hedgehog signaling pathway agonist, and 2) an undifferentiation maintenance factor in the absence of feeder cells, (B) a step of subjecting the cultured pluripotent stem cells to suspension culture in serum-five medium to form a cell aggregate, (C) a step of further subjecting the cell aggregate obtained in step (B) to suspension culture in a culture medium containing a BMP signaling pathway agonist.

This method is also disclosed in, for example, WO 2016/063985 and WO 2017/183732, and can be referred to WO 2016/063985 and WO 2017/183732 for more details.

The TGFβ family signaling pathway inhibitor represents a substance that inhibits TGFβ family signaling pathways, i.e., signaling pathways, transduced by Smad family. Specific examples of the TGFβ family signaling pathway inhibitor include TGFβ signaling pathway inhibitors (e.g., SB431542, LY-364947, SB-505124, A-83-01), Nodal/Activin signaling pathway inhibitors (e.g., SB431542, A-83-01), and BMP signaling pathway inhibitors (e.g., LDN193189, Dorsomorphin). These substances are commercially available.

The sonic hedgehog (hereinafter sometimes referred to as "Shh") signaling pathway agonist represents a substance that can enhance signaling mediated by Shh. Examples of the Shh signaling pathway agonist include PMA (Purmorphamine) and SAG (Smoothened Agonist).

The concentration of the TGFβ family signaling pathway inhibitor and the sonic hedgehog signaling pathway agonist may be any concentration that can induce differentiation into retinal cells. For example, SB431542 is usually used at a concentration of 0.1 to 200 μM, preferably 2 to 50 μM. A-83-01 is usually used at a concentration of 0.05 to 50 μM, preferably 0.5 to 5 μM. LDN193189 is usually used at a concentration of 1 to 2000 nM, preferably 10 to 300 nM. SAG is usually used at a concentration of 1 to 2000 nM, preferably 10 to 700 nM. PMA is usually used at a concentration of 0.002 to 20 μM, preferably 0.02 to 2 μM.

In culturing pluripotent stem cells under feeder-free conditions in step (A), it is preferred that the above-mentioned feeder-free medium containing an undifferentiation maintenance factor is used as the culture medium.

In culturing pluripotent stem cells under feeder-free conditions in step (A), an appropriate matrix may be used as a scaffold in order to provide the pluripotent stem cells with a scaffold instead of feeder cells. Examples of the matrix that can be used as a scaffold include laminin (Nat Biotechnol 28, 611-615, (2010)), laminin fragments (Nat Commun 3, 1236, (2012)), basement membrane preparation (Nat Biotechnol 19, 971-974, (2001)), gelatin, collagen, heparan sulfate proteoglycan, entactin, and vitronectin.

The culture time of the pluripotent stem cells in step (A) is not particularly limited to the extent that an effect of improving the quality of the cell aggregates formed in step (B) can be achieved, but it is typically 0.5 to 144 hours. In one embodiment, the culture time is preferably 2 to 96 hours, more preferably 6 to 48 hours, further preferably 12 to 48 hours, and still more preferably 18 to 28 hours (e.g., 24 hours).

Preparation of the serum-five medium and formation of the cell aggregate can be performed in the same manner as described above.

In one embodiment, the culture medium used in step (B) contains a sonic hedgehog signaling pathway agonist. As the sonic hedgehog signaling pathway agonist, the above-mentioned sonic hedgehog signaling pathway agonist can be used at the above-mentioned concentration. The sonic hedgehog signaling pathway agonist is preferably contained in the culture medium from the start of suspension culture. A ROCK inhibitor (for example, Y-27632) may be added to the culture medium. The culture time is, for example, 12 hours to 6 days.

The BMP signaling pathway agonist represents a substance that can enhance a signaling pathway mediated by BMP. Examples of the BMP signaling pathway agonist include BMP proteins such as BMP2, BMP4 or BMP7, GDF proteins such as GDF7, anti-BMP receptor antibodies, and BMP partial peptides. BMP2 protein, BMP4 protein and BMP7 protein are available from, for example, R&D Systems, Inc., and GDF7 protein is available from, for example, Wako Pure Chemical Industries, Ltd.

Examples of the culture medium to be used include a serum-free medium or a serum medium (preferably a serum-free medium) supplemented with a BMP signaling pathway agonist. The serum-free medium and serum medium can be prepared as described above.

The concentration of the BMP signaling pathway agonist may be a concentration capable of inducing differentiation into retinal cells. For example, when the BMP signaling pathway agonist is human BMP4 protein, the human BMP4 protein is added to the culture medium at concentration of about 0.01 nM to about 1 μM, preferably about 0.1 nM to about 100 nM, more preferably about 1 nM to about 10 nM, furthermore preferably at about 1.5 nM (55 ng/mL).

The BMP signaling pathway agonist has only to be added after about 24 hours from the start of suspension culture in step (A), and may be added to the culture medium within several days (for example, within 15 days) after the start of suspension culture. Preferably, the BMP signaling pathway agonist is added to the culture medium between day 1 and day 15, more preferably between day 1 and day 9, and most preferably on day 3 after the start of suspension culture.

As a specific embodiment, for example, a part or all of the culture medium may be replaced with a culture medium containing BMP4 at day 1 to day 9, preferably day 1 to day 3 after the start of the suspension culture in step (B), and the final concentration of BMP4 may be adjusted to about 1 to 10 nM, and the cells may be cultured in the presence of BMP4, for example, for 1 to 12 days, preferably 2 to 9 days, more preferably 2 to 5 days. Here, in order to maintain the same concentration of BMP4, a part or all of the medium can be replaced once or twice with a medium containing BMP4. Alternatively, the concentration of BMP4 can be decreased stepwise.

Culture conditions in the steps (A) to (C), such as culture temperature or $CO_2$ concentration can be set appropriately.

The culture temperature is, for example, about 30° C. to about 40° C., preferably about 37° C. In addition, the $CO_2$ concentration is, for example, from about 1% to about 10%, preferably about 5%.

By varying the culture period in step (C), retinal cells at various differentiation stages can be produced as retinal cells contained in the cell aggregates of neural retina. That is, the retinal cells in the cell aggregate of neural retina containing immature retinal cells (e.g., retinal progenitor cells, photoreceptor progenitor cells) and mature retinal cells (e.g., photoreceptor cells) in various proportions can be produced. By extending the culture period in step (C), it is possible to increase the proportion of mature retinal cells.

For step (B) and/or step (C), the method disclosed in WO 2017/183732 can also be used. That is, in step (B) and/or step (C), the cells are subjected to suspension culture in a culture medium further containing a Wnt signaling pathway inhibitor to form a cell aggregate of neural retina.

The Wnt signaling pathway inhibitor used in step (B) and/or step (C) is not particularly limited as long as it can suppress signaling mediated by Wnt, and the Wnt signaling pathway inhibitor may be protein, nucleic acid, low molecular weight compound, or the like. Signals mediated by Wnt are transduced through Wnt receptors that exist as heterodimers of Frizzled (Fz) and LRP5/6 (low-density lipoprotein receptor-related protein 5/6). Examples of the Wnt signaling pathway inhibitor include, but are not limited to, substances that act directly on Wnt or Wnt receptors (e.g., anti-Wnt neutralizing antibodies, anti-Wnt receptor neutralizing antibodies); substances that suppress expression of genes encoding Wnt or Wnt receptors (e.g., antisense oligonucleotides, siRNA); substances that inhibit Wnt receptor-Wnt binding (e.g., soluble Wnt receptors, dominant negative Wnt receptors, Wnt antagonists, Dkk1, Cerberus proteins); and substances that inhibit physiological activity caused by signaling by Wnt receptors [e.g., low molecular compounds such as CKI-7 (N-(2-aminoethyl)-5-chloroisoquinoline-8-sulfonamide), D4476 (4-[4-(2,3-Dihydro-1,4-benzodioxin-6-yl)-5-(2-pyridinyl)-1H-imidazol-2-yl]benzamide), IWR-1-endo (IWR1e)(4-[(3 aR,4S,7R,7aS)-1,3,3a,4,7,7a-hexahydro-1,3-dioxo-4,7-methano-2H-isoindol-2-yl]-N-8-quinolinyl-benzamide), and IWP-2 (N-(6-methyl-2-benzothiazolyl)-2-[(3,4,6,7-tetrahydro-4-oxo-3-phenylthieno [3,2-d]pyrimidin-2-yl) thio]acetamide). One or two or more of these may be included as the Wnt signaling pathway inhibitor. CKI-7, D4476, IWR-1-endo (IWR1e), IWP-2 or the like are known Wnt signaling pathway inhibitors, and commercially available. IWR1e is preferably used as the Wnt signaling pathway inhibitor.

The concentration of Wnt signaling pathway inhibitor in step (B) may be a concentration capable of inducing good cell aggregate formation. For example, when IWR-1-endo is used as the Wnt signaling pathway inhibitor, IWR-1-endo is added to the culture medium at a concentration from about 0.1 µM to about 100 µM, preferably from about 0.3 µM to about 30 µM, more preferably from about 1 µM to about 10 µM, even more preferably about 3 µM. When a Wnt signaling pathway inhibitor other than IWR-1-endo is used, it is desirable to use the Wnt signaling pathway inhibitor at a concentration that exhibits Wnt signaling pathway inhibitory activity equivalent to that of IWR-1-endo at the concentration described above.

In step (B), it is better that the timing of adding the Wnt signaling pathway inhibitor to the culture medium is earlier. The Wnt signaling pathway inhibitor is added to the culture medium usually within 6 days, preferably within 3 days, more preferably within 1 day, more preferably within 12 hours from the start of suspension culture in step (B), furthermore preferably at the start of suspension culture in step (B). Specifically, for example, a basal medium supplemented with a Wnt signaling pathway inhibitor can be added, or the replacement of a part or all of the medium with the basal medium can be performed. The period during which the cells obtained in step (A) are acted on the Wnt signaling pathway inhibitor in step (B) is not particularly limited, but preferably, the Wnt signaling pathway inhibitor are added to the culture medium at the start of suspension culture in step (B), then the cells are acted on the Wnt signaling pathway inhibitor until the end of step (B) (immediately before the addition of the BMP signaling pathway agonist). More preferably, as described later, the cells are exposed to the Wnt signaling pathway inhibitor continuously even after the completion of the step (B) (that is, during the period of the step (C)). In one embodiment, as described later, the cells are continuously acted on the Wnt signaling pathway inhibitor even after the completion of the step (B) (that is, during the period of the step (C)) until a retinal tissue is formed.

In the step (C), as the Wnt signaling pathway inhibitor, any of the aforementioned Wnt signaling pathway inhibitors can be used, but preferably, the same type of Wnt signaling pathway inhibitor used in step (B) is used in step (C).

The concentration of Wnt signaling pathway inhibitor in step (C) has only to be a concentration capable of inducing a retinal progenitor cell and retinal tissue. For example, when IWR-1-endo is used as the Wnt signaling pathway inhibitor, IWR-1-endo is added to the culture medium at a concentration of from about 0.1 µM to about 100 µM, preferably from about 0.3 µM to about 30 µM, more preferably from about 1 µM to about 10 µM, even more preferably about 3 µM. When a Wnt signaling pathway inhibitor other than IWR-1-endo is used, it is desirable to use the Wnt signaling pathway inhibitor at a concentration that exhibits Wnt signaling pathway inhibitory activity equivalent to that of IWR-1-endo at the concentration described above. The concentration of the Wnt signaling pathway inhibitor in the culture medium of step (C) is preferably 50 to 150, more preferably 80 to 120, furthermore preferably 90 to 110, when the concentration of Wnt signaling pathway inhibitor in step (B) is 100. It is more preferred that the concentration of Wnt signaling pathway inhibitor in step (C) is equivalent to the concentration of the Wnt signaling pathway inhibitor in the culture medium of the second step.

The timing of adding the Wnt signal transduction pathway inhibitor to the culture medium is not particularly limited as long as aggregate formation including retinal cells or retinal tissue can be achieved, but earlier timing is better. Preferably, the Wnt signaling pathway inhibitor is added to the culture medium at the start of step (C). More preferably, after the Wnt signaling pathway inhibitor is added in step (B), the Wnt signaling pathway inhibitor is continuously contained in the culture medium in step (C) (i.e., from the start of step (B)). More preferably, after the Wnt signaling pathway inhibitor is added at the start of suspension culture in step (B), the Wnt signaling pathway inhibitor is continuously contained in the culture medium in step (C). For example, a BMP signaling pathway agonist (e.g., BMP4) may be added to the culture obtained in step (B) (a suspension of aggregates in the culture medium containing a Wnt signaling pathway inhibitor).

The period for being acted on the Wnt signaling pathway inhibitor is not particularly limited, but preferably, in the case that the Wnt signaling pathway inhibitor is added at the start of suspension culture in step (B), the period is 2 to 30 days, more preferably 6 to 20 days, 8 to 18 days, 10 to 18 days, or 10 to 17 days (for example, 10 days) starting from the start of suspension culture in step (B). In another embodiment, the period for being acted on the Wnt signaling pathway inhibitor is, in the case that the Wnt signaling pathway inhibitor is added at the start of suspension culture in step (B), preferably 3 to 15 days (e.g., 5 days, 6 days, 7 days), more preferably 6 to 10 days (e.g., 6 days) starting from the start of suspension culture in step (B).

Neural retina containing ciliary marginal zone-like structure can also be produced by culturing cell aggregates of neural retina obtained in the methods described above in serum-free medium or serum medium containing a Wnt signaling pathway agonist and/or FGF signaling pathway inhibitor for a period of about 3 to 6 days (step (D)); followed by culturing in serum-free medium or serum medium not containing a Wnt signaling pathway agonist and/or FGF signaling pathway inhibitor for about 30 to 60 days (step (E)).

In one embodiment, neural retina containing ciliary marginal zone-like structure can be produced by the above-described steps (D) and (E) from the cell aggregates of neural retina obtained in steps (A) to (C) on days 6-30, days 10-20 (days 10, 11, 12, 13, 14, 15, 16, 17, 18, 19, or 20) following the start of suspension culture in step (B).

The Wnt signaling pathway agonist is not particularly limited as long as it can enhance signaling mediated by Wnt. Specific examples of the Wnt signaling pathway agonist include GSK3β inhibitors (e.g., 6-Bromoindirubin-3'-oxime (BIO), CHIR99021, Kenpaullone). For example, when the Wnt signaling pathway agonist is CHIR99021, a range thereof can be about 0.1 µM to about 100 µM, preferably about 1 µM to about 30 µM.

The FGF signaling pathway inhibitor is not particularly limited as long as it can inhibit signaling mediated by FGF. Examples of the FGF signaling pathway inhibitor include SU-5402, AZD4547, and BGJ398. For example, when the FGF signaling pathway inhibitor is SU-5402, it is added at a concentration of about 0.1 µM to about 100 µM, preferably about 1 µM to about 30 µM, more preferably about 5 µM.

The cell aggregate of neural retina can be produced by the above-described method, but is not limited thereto.

(Retinal Pigment Epithelial Cells)

It is preferred that retinal pigment epithelial cells are derived from pluripotent stem cells. Examples of methods for preparing retinal pigment epithelial cells from pluripotent stem cells include, but are not particularly limited to, those disclosed in WO 2012/173207, WO 2015/053375, WO 2015/053376, WO 2015/068505, WO 2017/043605, Stem Cell Reports, 2(2), 205-218 (2014) and Cell Stem Cell, 10(6), 771-785 (2012). It is also possible to prepare an aggregate of retinal pigment epithelial cells by improving the method described in WO 2016/063985 described above. Retinal pigment epithelial cells may be prepared as a cell sheet or cell suspension.

As a modification of the method described in WO 2006/063985, among the methods described above, pluripotent stem cells are cultured in the absence of feeder cells under conditions where 1) they are subjected to treatment with a TGFβ family signaling pathway inhibitor and sonic hedgehog signaling pathway agonist one day prior to differentiation induction, and 2) they are not subjected to treatment with sonic hedgehog signaling pathway agonists at the start of differentiation induction. Thereafter, steps (B) and (C) described above are performed. Furthermore, it is preferred to advance the start time of step (D). Specifically, step (D) is started about 9 days from (for example, 7 days, 8 days, 9 days, 10 days, and 11 days after) the start of suspension culture in step (B). Subsequently, step (E) described above may be performed.

Retinal pigment epithelial cells may be further cultured until they have a polygonal or cobblestone-like cell morphology prior to contact with the cell aggregate of neural retina. The culture medium in this case is not particularly limited, but the cells can be further cultured after replacing the medium with a retinal pigment epithelial cell maintenance medium (hereinafter sometimes referred to as RPE maintenance medium). This allows for more explicit observation of a group of melanized cells or a group of cells with polygonal squamous morphology which adhere to the basement membrane. The culture using the RPE maintenance medium is not limited as long as colonies of retinal pigment epithelial cells are formed, but, for example, the culture is performed for about 5 to 20 days while replacing the whole medium at least once every 3 days. Those skilled in the art can easily set the culture period while confirming the form. As the maintenance medium for retinal pigment epithelial cells, the medium, for example, described in IOVS, March 2004, Vol. 45, No. 3, Masatoshi Haruta et al., IOVS, November 2011, Vol. 52, No. 12, Okamoto et al., Cell Science 122(17), Fumitaka Osakadar et al., February 2008, Vol. 49, No. 2, Gamin et al. can be used.

Those skilled in the art can also prepare a cell suspension of retinal pigment epithelial cells by conventional methods such as pipetting from aggregates or cell sheets of retinal pigment epithelial cells obtained by the methods described above. For example, the aggregate or a cell sheet is washed with PBS (manufactured by Thermo Fisher Scientific, Inc.) or the like, then treated with a cell dissociating enzyme such as TrypLE™ Select (manufactured by Thermo Fisher Scientific, Inc.) for about 15 to 30 minutes, and pipetting is performed to prepare a cell suspension. It may also be passed through a mesh such as a cell strainer.

The "cell sheet" refers to a monolayer or multilayer structure constituted by single or a plurality of cells having biological connections in at least two dimensions. Cell sheets can be made by cutting out from adhesively cultured cells or cell aggregates using forceps, knife, scissors, or the like.

The "cell suspension" means a solution containing a plurality of cells of the same type or different types in a suspended state. Preferably, the majority (e.g., 50% or more, 60% or more, 70% or more, 80% or more, 90% or more, or 95% or more) of cells present in the medium dissociate from each other and exist without sustained physical contact. Some other cells may exist as cell aggregates and the like.

Cell suspensions of retinal pigment epithelial cells can be prepared, for example, by dispersing retinal pigment epithelial cells manufactured as a cell sheet or cell aggregate into single cells. The method for dispersion is not particularly limited, but it can be dispersed by methods well known to those skilled in the art, such as chemical treatment with cell dissociation enzymes (e.g., TrypLE™ Select, by Thermo Fisher Scientific, Inc.) or physical treatment with self-scrapers, and the like.

(Contacting Step)

Methods of contacting the cell aggregate of neural retina with the retinal pigment epithelial cell is not particularly limited as long as the cell aggregate of neural retina and the retinal pigment epithelial cell can adhere to each other. Examples thereof include a method of culturing the cell aggregate of neural retina with a suspension of the retinal pigment epithelial cells and adhering the retinal pigment epithelial cells to the cell aggregate of neural retina sunk to the bottom of a plate, or a method of contacting the cell aggregate of neural retina with a retinal pigment epithelial cell sheet; and the method of utilizing osmotic pressure difference.

The method of culturing the cell aggregate of neural retina with a suspension of the retinal pigment epithelial cells and adhering the retinal pigment epithelial cells to the cell aggregate of neural retina sunk to the bottom of a culture container such as a plate is preferably performed in a low adhesion container so that adhesion of retinal pigment epithelial cells to the culture container does not affect the adhesion to the cell aggregate. Examples of the container include a small-well plate (for example, a plate in which the bottom area of well is 0.1 to 2.0 cm$^2$ in terms of a flat bottom), a means confining cells in a small space using a micropore or the like, and a small centrifuge tube. Examples of the small-well plate include, for example, a 24-well plate (the area is approximately 1.88 cm$^2$ in terms of a flat bottom), a 48-well plate (the area is approximately 1.0 cm$^2$ in terms of a flat bottom), a 96-well plate (the area is approximately 0.35 cm$^2$ in terms of a flat bottom), and a 384 well plate. As the shape of the small-well plate, the shape of the bottom surface when the well is viewed from the side may be a flat bottom structure or a structure in which the outer peripheral portion is high and the inner convex portion is recessed. Examples of the shape of the bottom surface include U-bottom, V-bottom, M-bottom, and flat-bottom. The bottom surface of the small-well plate is preferably a non-cell-adhesive bottom surface, preferably Prime surface (manufactured by Sumitomo Bakelite Co., Ltd.). As a non-cell-adhesive culture container, a culture container of which the surface is artificially treated (for example, by super hydrophilic treatment with MPC polymer or the like, or by low protein adsorption treatment) for the purpose of reducing the adhesion to cells can be used.

Other examples include a method of adhering the cells by agitation culture using a bioreactor and the like.

It is preferred that the culture is performed in a manner that the cell aggregate of neural retina is deposited to the bottom of the well so that the retinal pigment epithelial cells adhere to the entire surface of the cell aggregate of neural retina.

The concentration of the cell suspension of retinal pigment epithelial cells and the culture period for adhesion can be easily set by those skilled in the art by confirming the adhesion and proliferation of RPE cells. The adhesion of the retinal pigment epithelial cells to the surface of the cell aggregate of neural retina can be confirmed by, for example, microscopic observation or immunostaining. Furthermore, the proliferation of retinal pigment epithelial cells adhered to the surface of the cell aggregate of neural retina can be confirmed, for example, by microscopic observation or immunostaining. The concentration of the cell suspension of retinal pigment epithelial cells is, specifically, $1 \times 10^4$ cells or more per well, preferably $1 \times 10^5$ cells or more per cell. The culture period for adhesion is 1 to 60 days, preferably 3 to 30 days.

It is preferred that the cell aggregate of neural retina are coated with an adhesion factor (e.g., an extracellular matrix) described later prior to contacting the cell aggregate of neural retina with the retinal pigment epithelial cells. The culture of cell aggregates of neural retina and retinal pigment epithelial cells may be performed in the presence of an adhesion factor.

Examples of the method of contacting the cell aggregate of neural retina or a cell sheet that is a portion thereof with a retinal pigment epithelial cell sheet include a method of causing the cell aggregate of neural retina or a cell sheet of neural retina obtained by cutting out the cell aggregate of neural retina to sink onto an adhesively cultured retinal pigment epithelial cell sheet by self-weight or overlaying a mesh, and to stick on.

It is preferred that an adhesion factor (e.g., extracellular matrix) described later are coated on the retinal pigment epithelial cell sheet prior to contacting the cell sheet of neural retina with the retinal pigment epithelial cell sheet.

In the method of utilizing osmotic pressure differences, the cell aggregate of neural retina and retinal pigment epithelial cells are contacted with each other and cultured, for example, in a medium containing methylcellulose. Specifically, the cell aggregate of neural retina containing neural retina are floated in a medium containing 0.1% to 20% (e.g., 3%) methylcellulose, and retinal pigment epithelial cells suspended in a medium at 1000 cells/μL to 1000000 cells/μL are slowly ejected in small amounts (1 μL to 10 μL, e.g., 3 μL) to the cell aggregate of neural retina in the medium containing methylcellulose. This procedure allows for formation of droplets of the medium containing retinal pigment epithelial cells around the cell aggregates of neural retina, and, by culturing for a period of time (e.g., about 1 hour), only the medium in the droplets diffuses into external liquid due to the difference of osmotic pressure from the medium containing methylcellulose, thereby facilitating adhesion by aggregating retinal pigment epithelial cells around the cell aggregates of neural retina. Hydrogels and the like can also be used instead of methylcellulose.

The medium used in the above-described three contact methods is not particularly limited, but examples thereof include a medium used for culturing retinal cells, retinal pigment epithelial cells, or neural retina (e.g., DMEM/F12 medium, Neurobasal™ medium, a mixed medium of these, RPE maintenance medium). It is also preferred that the medium includes the adhesion factor described later.

In the contacting step, it is preferred that they are contacted in the presence of an adhesion factor. The adhesion factor means a substance that has an effect of achieving adhesion between cells, and examples thereof include, but are not limited to, extracellular matrix and artificial hydrogels described above. The adhesion factor need not be an isolated single substance, and examples thereof also include Matrigel®, inter-photoreceptor cell matrix, and a preparation from living organisms or cells, such as serum. Matrigel® is a basement membrane preparation from Engelbreth Holm Swam (EHS) mouse sarcoma. Matrigel® can be prepared, for example, by the methods disclosed in U.S. Pat. No. 4,829,000 and can also be purchased commercially. The main components of Matrigel® are laminin, type IV collagen, heparan sulfate proteoglycan and entactin. The interphotoreceptor matrix is a general term for an extracellular matrix that exists between retinal cells such as photoreceptor cell and the like in a retina in vivo, and examples thereof include hyaluronic acid. The interphotoreceptor matrix can be harvested from a retina in vivo by those skilled in the art, for example, by placing retina in distilled water, and expanding and separating interphotoreceptor matrix, and can also be purchased commercially. Preferably the adhesion factor is an extracellular matrix, and further preferably the extracellular matrix includes one or more extracellular matrices selected from the group consisting of hyaluronic acid, laminin, type IV collagen, heparan sulfate proteoglycan and entactin. The contact may also be performed in the presence of an extracellular matrix together with other components such as growth factors, for example, EGF. Examples of commercially available extracellular matrix include Matrigel® and iMatrix® 511.

The concentration of the extracellular matrix in the contacting step varies depending on the size of the cell aggregate of neural retina and the number of retinal pigment epithelial cells, but those skilled in the art can be easily set the concentration by confirming the adhesion and proliferation of RPE cells. For example, when the extracellular matrix is Matrigel®, it is preferably added at a concentration of 200-10000 times diluted ready-made products (Becton, Dickinson (BD) and Company), and in the case of iMatrix® 511, at a concentration of 0.1-5 ug/ml.

Specifically, the culture for adhering the cell aggregates of neural retina to the retinal pigment epithelial cells may be performed in a medium containing an adhesion factor. They may be continuously cultured in the above medium containing an adhesion factor during the culture period for adhering the cell aggregate of neural retina to the retinal pigment epithelial cells described above. They may also be cultured for a certain period of time (e.g., 1 day to 10 days) in the above medium containing an adhesion factor, then may be continuously cultured after the medium was replaced with an adhesion factor-free media.

The cell aggregate of neural retina or retinal pigment epithelial cell sheet may be coated with the adhesion factor prior to the culture for adhering the cell aggregate of neural retina to the retinal pigment epithelial cells. Specifically, the cell aggregate of neural retina or the retinal pigment epithelial cell sheet may be cultured in the above medium containing an adhesion factor. Those person skilled in the art can set the culture time as appropriate, and the culture may be performed for about 10 minutes to 5 hours (e.g., 10 minutes to 60 minutes). After the culture, they may be washed with a medium such as PBS.

For the cell aggregate of neural retina containing neural retina and the retinal pigment epithelial cells to be contacted, when the cell aggregate of neural retina and the retinal pigment epithelial cells having different culture days in the above production method are used, the dates of starting the production may be shifted. When the retinal pigment epithelial cells are an aggregate or cell sheet, the aggregate or cell sheet may be subjected to cell dissociation enzyme treatment and/or pipetting procedure to dissociate the cells and be prepared as a cell suspension of retinal pigment epithelial cells prior to be contacted with the cell aggregates of neural retina.

By contacting the cell aggregates of neural retina with the retinal pigment epithelial cells, both are adhered to form a sphere-like cell aggregate comprising a core part and a covering part. After contacting the cell aggregate of neural retina with retinal pigment epithelial cells, it is preferred to perform further culture such that the cell aggregate of neural retina and the retinal pigment epithelial cells adhere to each other, the retinal pigment epithelial cells cover the entire surface of the cell aggregates of neural retina, and/or the retinal pigment epithelial cells have a polygonal or cobblestone-like cell morphology. The culture medium to be used is not particularly limited to the extent that the above objective can be achieved, but examples thereof include those used in the culture of retinal cells, retinal pigment epithelial cells, or neural retina (e.g., DMEM/F12 medium, Neurobasal™ medium, a mixed medium of these, RPE maintenance medium). Those skilled in the art can confirm under a microscope the state of cell adhesion and the proportion of the retinal pigment epithelial cells present on the surface of the cell aggregate of neural retina. Furthermore, those skilled in the art can confirm whether retinal pigment epithelial cells have a polygonal or cobblestone-like cell morphology, and can set the period of culture days by confirming the shape. After performing the contacting step described above, the culture may be performed in a range of about 1 day to 100 days (5 days to 50 days).

[Reagent for Evaluating Toxicity or Drug Efficacy and Method for Evaluating Toxicity or Drug Efficacy of Test Substance]

A reagent for evaluating toxicity or drug efficacy of a test substance according to one embodiment of the present invention contains the sphere-like cell aggregate according to one embodiment of the present invention or a portion of the cell aggregate. A method for evaluating toxicity or drug efficacy of a test substance according to one embodiment of the present invention comprises contacting the sphere-like cell aggregate according to one embodiment of the present invention or a portion of the cell aggregate with the test substance, and examining an effect of the test substance on the sphere-like cell aggregate or a cell contained in the sphere-like cell aggregate.

For example, iPS cells are made from human patients having diseases based on retinal tissue disorders, particularly diseases based on hereditary disorders, and a sphere-like cell aggregate is produced by using the iPS cells according to the methods according to the present invention. The sphere-like cell aggregate can reproduce in vitro the disorder of retinal tissue that causes the disease afflicting the patient. Accordingly, the present invention provides a method for evaluating toxicity or drug efficacy of a test substance, comprising contacting the sphere-like cell aggregate produced by the production method according to the present invention with a test substance, and examining an effect of the test substance on the sphere-like cell aggregate or a cell contained in the sphere-like cell aggregate.

[Treatment Drug, Treatment Method and Pharmaceutical Composition]

A treatment drug according to one embodiment of the present invention is a drug for treating a disease based on a disorder of a retinal pigment epithelial cell, a retinal cell or a retinal tissue or a damage of a retinal tissue, particularly for serious instances in which both photoreceptor cells and retinal pigment epithelial cells are simultaneously impaired or damaged, comprising the sphere-like cell aggregate or a portion of the cell aggregate. A treatment method according to one embodiment of the present invention is a method for treating a disease based on a disorder of a retinal pigment epithelial cell, a retinal cell or a retinal tissue or a damage of a retinal tissue, particularly for serious instances in which both photoreceptor cells and retinal pigment epithelial cells are simultaneously impaired or damaged, comprising transplanting an effective amount of the sphere-like cell aggregate or a portion of the sphere-like cell aggregate into a subject in need of transplantation. A pharmaceutical composition according to one embodiment of the present invention contains the sphere-like cell aggregate according to the present invention or a portion thereof as an active ingredient. The pharmaceutical composition according to one embodiment of the present invention is useful as a drug for treating a disease based on a disorder of a retinal pigment epithelial cell, a retinal cell or a retinal tissue or a damage of a retinal tissue, particularly for serious instances in which both photoreceptor cells and retinal pigment epithelial cells are simultaneously impaired or damaged.

Examples of the disease based on a disorder of retinal tissue include macular degeneration, aging macular degeneration, retinal pigmentation, glaucoma, corneal disease, retinal detachment, central serous retinopathy, cone dystrophy, and rod-cone dystrophy, which are ophthalmic diseases. Examples of the state of damage of retinal tissue include a state in which photoreceptor cells are degenerative dead.

The treatment drug or pharmaceutical composition according to one embodiment of the present invention may comprise an effective amount of a sphere-like cell aggregate or a portion of the cell aggregate, and a pharmaceutically acceptable carrier. An effective amount of the sphere-like cell aggregate for transplantation may vary depending on the purpose of administration, method of administration, circumstance of administration subject (gender, age, weight, medical condition, or the like), but examples thereof include $1\times10^5$, $1\times10^6$ or $1\times10^7$ cells as the number of cells.

As the pharmaceutically acceptable carrier, a physiological aqueous solvent (physiological saline, buffer solution, serum-free medium, or the like) can be used. As necessary, medicines containing a tissue or cells to be transplanted in transplantation therapy may be blended with a preservative, a stabilizer, a reducing agent, an isotonic agent and the like which are usually used.

The treatment drug or pharmaceutical composition according to one embodiment of the present invention can be produced as a cell suspension by suspending the sphere-like cell aggregate according to the present invention or a portion of the cell aggregate in an appropriate physiological aqueous solvent. If necessary, after addition of a cryopreservation agent, the cell suspension may be cryopreserved, thawed upon use, washed with a buffer, and used for transplantation therapy.

In one embodiment, the sphere-like cell aggregate according to the present invention can be sliced in an appropriate size using forceps, a knife, scissors, or the like, thereby cut out and utilized to transplant a portion of the aggregate. The shape after cut out is not particularly limited, but examples thereof include a cell sheet.

[Portion of Sphere-Like Cell Aggregate and Method for Producing the Same]

The portion of the sphere-like cell aggregate according to one embodiment of the present invention is a portion of the sphere-like cell aggregate according to the present invention and can be obtained, for example, by physically cutting out from the sphere-like cell aggregate according to the present invention. The shape of the portion of the sphere-like cell aggregate is not particularly limited, and may not be a sphere-like shape. A portion of the sphere-like cell aggregate is a cell aggregate comprising neural retina and a covering containing retinal pigment epithelial cells in contact with each other that continuously or discontinuously covers at least a portion of the surface of the neural retina, and may be, for example, a cell sheet comprising retinal pigment epithelial cells and neural retina.

The method for producing the portion of the sphere-like cell aggregate according to one embodiment of the present invention comprises a step of physically cutting out a portion of the sphere-like cell aggregate according to the present invention. The cutting out step can be performed by conventional methods, for example, a method of slicing in an appropriate size using forceps, a knife, scissors, or the like.

EXAMPLES

Hereinafter, the present invention is described in detail with reference to examples, but the present invention is not limited thereto.

Example 1 Separate Preparation of Retinal Pigment Epithelium (RPE) Cells and Neural Retina (NR)

Human ES cells genetically modified to have a Crx:: Venus reporter gene (Kh-ES1 strain, Cell Stem Cell, 10(6), 771-785, (2012)) were cultured under a feeder-free condition according to the method described in "Scientific Reports, 4, 3594 (2014). StemFit® medium (trade name: AK03N, manufactured by Ajinomoto Co., Inc.) was used as the feeder-free culture medium, and Laminin 511-E8 (trade name, manufactured by Nippi. Inc.) was used as a scaffold in stead of the feeder cells.

Specific maintenance and culturing procedures of human ES cells were performed as follows. First, human ES cells (KhES-1 strain) that has become sub-confluent (the state of approx. 60% of the culture area is covered with cells) were washed with PBS, and then dispersed into single cells with TrypLE™ Select (trade name, manufactured by Life Technologies Corporation). Human ES cells dispersed into single cells were then seeded in a Laminin 511-E8 coated plastic culture dish and cultured in the presence of Y27632 (ROCK inhibitor, 10 µM) in StemFit® medium under a feeder-free condition. When a 6-well plate (IWAKI, for cell culture, culture area 9.4 cm$^2$) was used as the plastic culture dish, the number of seeded cells of the human ES cells dispersed in the single cells was $1.2\times10^4$ cells per well. One day after the seeding, the medium was replaced with a StemFit® medium free of Y27632. Thereafter, the medium was replaced with once every 1 to 2 days with a StemFit® medium free of Y27632. Then, 6 days after the seeding, the cells were cultured until 1 day before becoming sub-confluent.

The human ES cells 1 day prior to the sub-confluent were cultured under a feeder-free condition for 1 day under the following two conditions: (1) in the presence of SAG (Shh signaling pathway agonist, 300 nM), or (2) in the presence of SAG and SB431542 (TGFβ signaling pathway inhibitor, 5 µM) (hereinafter, this treatment is also described as Precondition treatment).

After the precondition-treated human ES cells were washed with PBS, the cells were subjected to cell dispersion treatment with TrypLE™ Select, and further dispersed into single cells by pipetting procedure. Then, the human ES cells dispersed into single cells were suspended in 100 µL of serum-free medium in a non-cell-adhesive 96-well culture plate (trade name: PrimeSurface® 96-well V-bottom plate, manufactured by Sumitomo Bakelite Co., Ltd.) at $1.2\times10^4$ cells per well, and subjected to suspension culture at 37° C., 5% $CO_2$. The serum-free medium (gfCDM+KSR) used was a serum-free medium of a 1:1 mixture of F-12 medium and IMDM medium supplemented with 10% KSR, 450 µM 1-monothioglycerol, 1×Chemical Defined Lipid Concentrate.

At the start of suspension culture (day 0 after the start of suspension culture), Y27632 (ROCK inhibitor, final concentration 20 µM) was added to the above serum-free medium. At the same time, SAG (Shh signaling pathway agonist, 30 nM) was added or not added for examination. At day 3 after the start of suspension culture, 50 µL of culture medium containing foreign recombinant human BMP4 at a final concentration of 1.5 nM was added using a culture medium containing recombinant human BMP4 (trade name: Recombinant Human BMP-4, manufactured by R&D Systems Inc.) free of Y27632 and SAG.

On the days 3, 6, 9, 15, and 18 after the start of suspension culture of the cells thus prepared, one half of the medium was replaced with serum-free medium (gfCDM+KSR). Aggregates on the day 15 or 18 after the start of suspension culture were transferred to a 90 mm low-adhesive culture dish (manufactured by Sumitomo Bakelite Co., Ltd.), and cultured at 37° C., 5% $CO_2$ for 3-4 days in serum-free medium (DMEM/F12 medium supplemented with 1% N2 supplement) containing a Wnt signaling pathway agonist (CHIR99021, 3 μM) and an FGF signaling pathway inhibitor (SU5402, 5 μM). Subsequently, the aggregates were long-term cultured on a 90 mm low-adhesive culture dish (manufactured by Sumitomo Bakelite Co., Ltd.) in serum medium containing no Wnt signaling pathway agonists and FGF signaling pathway inhibitors (DMEM/F12 medium (manufactured by Thermo Fisher Scientific, Inc.) supplemented with 10% fetal bovine serum, 1% N2 supplement (manufactured by Thermo Fisher Scientific, Inc.) and Taurin: hereinafter sometimes referred to as NucT0 medium). One half of the medium was replaced with the serum medium once every 2 to 4 days. On the day 38 after the start of suspension culture, observation was performed with a microscope and a fluorescence microscope (FIG. 1).

As a result, RPE preparation efficiency was good when Precondition treatment with SAG and SB addition was performed and SAG was not added at the start of differentiation induction (FIGS. 1B, B'). Under the conditions other than the above, the preparation efficiency of the cell aggregate containing neural retina containing CRX positive photoreceptor progenitor cells was good (FIGS. 1A, A', C, C', D, D').

Example 2 Adhesion 1 Between NR and RPE Cells

RPE cells and NR prepared as in Example 1 each were long-term cultured after 40 days from the start of suspension culture in a serum medium free of Wnt signaling pathway agonists and FGF signaling inhibitors (medium in which NucT0 medium and NucT2 medium are mixed at a ratio of 1:3, hereinafter, the medium is sometimes referred to as NucT1 medium. The NucT2 medium means Neurobasal™ Medium (manufactured by Thermo Fisher Scientific, Inc.) supplemented with 10% FBS, B27 supplement w/o V.A. (manufactured by Thermo Fisher Scientific, Inc.), L-Glutamine, Taurin, and T3) until 59 days. After day 60 from the start of suspension culture, the cells were long-term cultured in a serum medium free of Wnt signaling pathway agonists and FGF signaling inhibitors (NucT2 medium).

Figure 2:
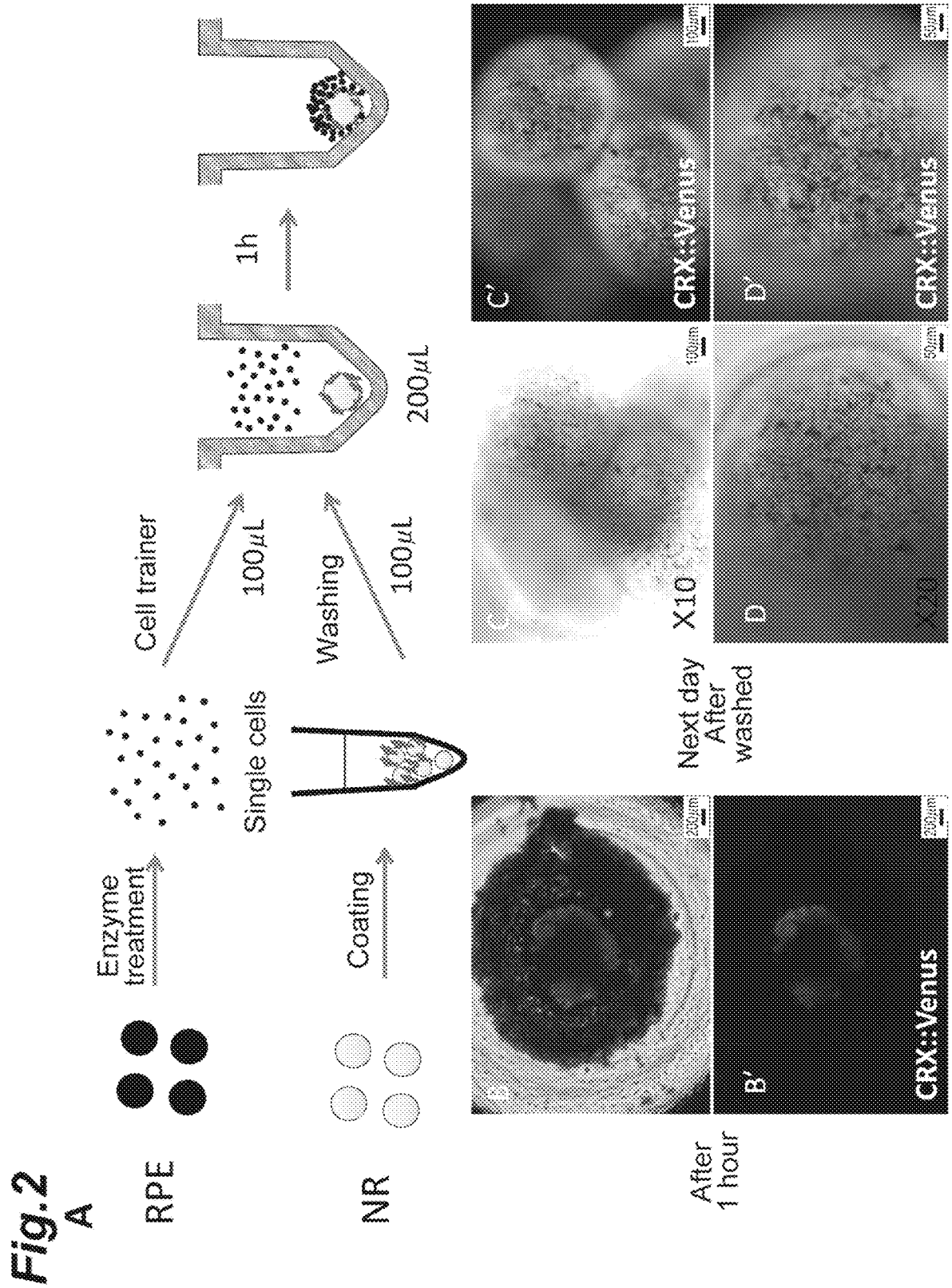
FIG. 2 is diagrams showing the method of adhering NR and RPE cells of Example 2 (A), and microscopic observation results (B, C, D) and fluorescence microscopic observation results (B', C', D') at 1 hour after adhesion and next day of adhesion.

RPE cells at day 80 to 90 and NR at day 50 to 120 after the start of suspension culture were respectively prepared, and respectively treated as follows (FIG. 2A).
RPE cells: After washed with PBS (manufactured by Thermo Fisher Scientific, Inc.), subjected to enzyme treatment with Tryple™ select (manufactured by Thermo Fisher Scientific, Inc.) for 15-30 minutes, then single-cell dissociated by pipetting, passed through 40 μm of cell strainer, and suspended in Nuc medium.
NR: NR was collected in a tube, coated with iMatrix® 511 (manufactured by Nippi. Inc.) or Matrigel® (manufactured by BD Company) for 15 to 60 minutes, and washed with PBS.
NR and RPE cells prepared as described above were seeded into a low-adhesive PrimeSurface® 96V plate (manufactured by Sumitomo Bakelite Co., Ltd.). One hour after the seeding, observation was performed with a microscope and a fluorescence microscope. As a result, it was confirmed that single-cell dissociated RPE cells were sunk to the bottom of the well and gathered around NR (FIGS. 2B, B'). Also, when washed with PBS next day and observed with a microscope and fluorescence microscope, it was confirmed that RPE cells adhered to the surface of NR (FIGS. 2C, C', D, D').

Figure 3:
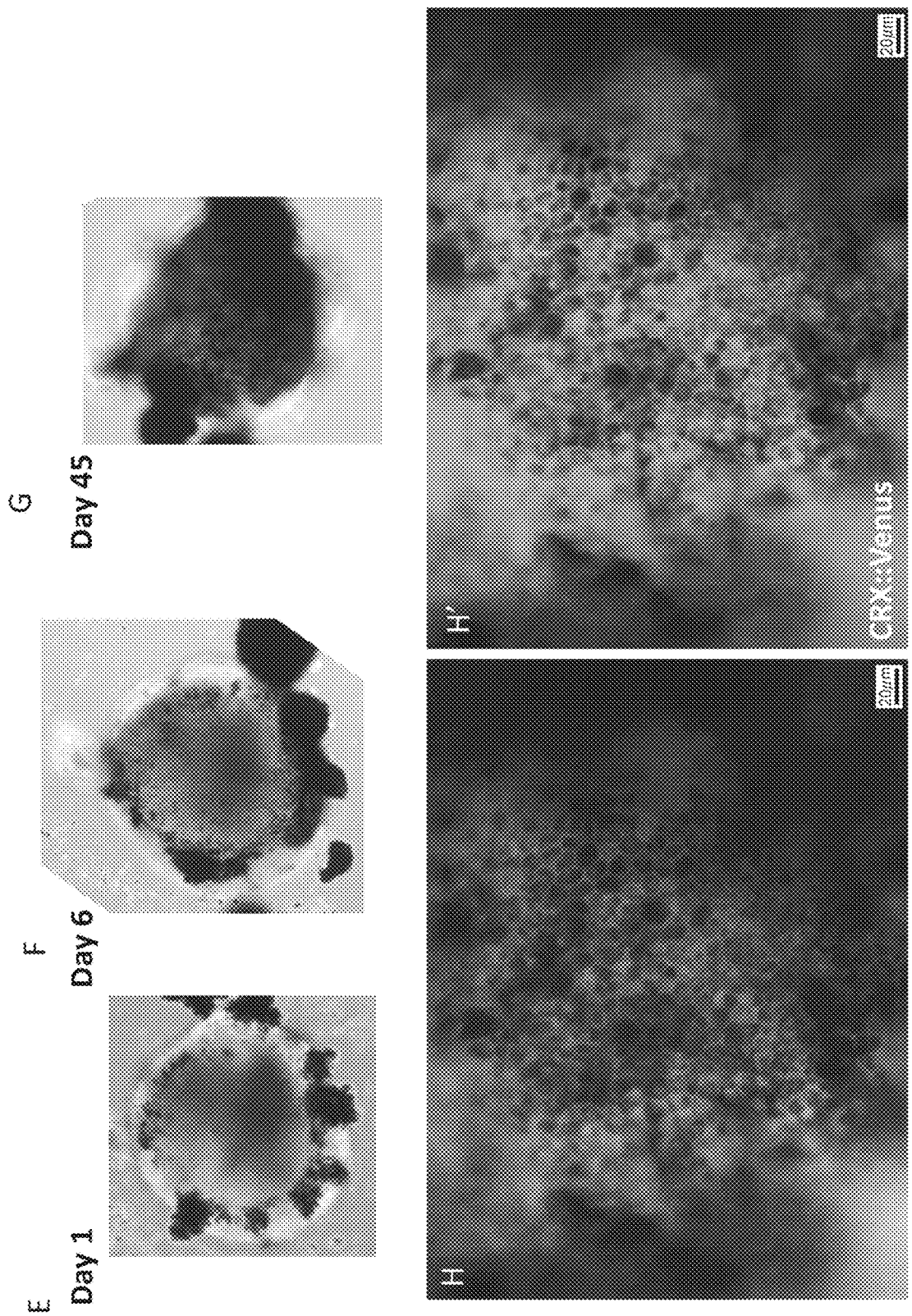
FIG. 3 is diagrams showing the results of observing changes over time at days 1, 6, and 45 after adhesion of NR and RPE cells in Example 2 with a microscope (E, F, G), and the results of observing morphology of RPE cells adhering to the NR surface at day 45 with a microscope (H) and with a fluorescence microscope (H').

Changes over time were observed on days 1, 6, and 45 after adhesion. As a result, it was confirmed by fluorescence microscopy that RPE cells adhered at day 1 gradually proliferated to begin covering the NR surface at day 6, and covered the NR surface at day 45 (FIGS. 3E, F, G). It was also confirmed by fluorescence microscopy that RPE cells adhering to the NR surface formed a hexagonal structure on day 45 (FIGS. 3H, H').

Figure 4:
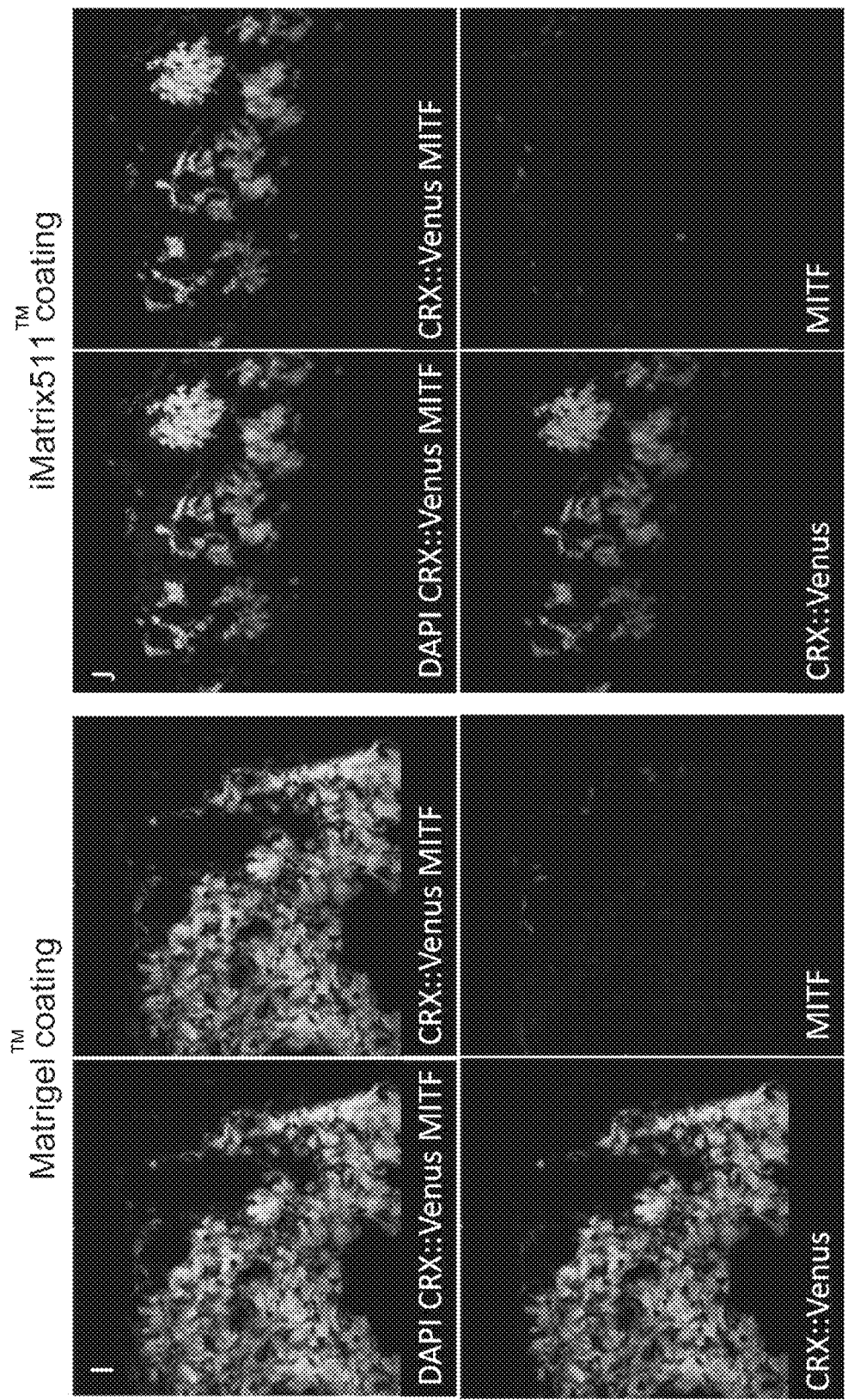
FIG. 4 is diagrams showing the results of immunostaining (cell) aggregates of NR-RPE cells at day 50 after adhesion of NR and RPE cells in Example 2 and observing with a confocal fluorescence microscope (I, J).

Cell aggregates of NR-RPE cells at day 50 after adhesion were immobilized with 4% PFA and frozen sections were prepared. With these frozen sections, immunostaining was performed on MITF protein using an anti-MITF antibody (trade name: Anti MITF Antibody, manufactured by Ex-alpha Biologicals, Inc.). These immunostained sections were observed with a confocal fluorescence microscope. As a result, it was confirmed that, MITF-positive RPE cells were localized on the surface of CRX-positive photoreceptor progenitor cells in the aggregate obtained by adhering NR and RPE cells (FIGS. 4I, J).

From these results, it was found that NR-RPE cell sheets in which RPE cells were localized on NR could be produced by adhering separately prepared RPE cells and NR.

Example 3 Adhesion 2 Between NR and RPE Cells

RPE cells and NR prepared as in Example 1 each were long-term cultured after day 40 from the start of suspension culture in a serum medium free of Wnt signaling pathway agonists and FGF signaling inhibitors (cultured in NucT1 medium which is a mixture of NucT0 medium and NucT2 medium at 1:3. NucT2 medium: Neurobasal™ Medium supplemented with 10% FBS, B27 supplement w/o V.A., L-Glutamine, Taurin, and T3) until 59 days. After day 60 from the start of suspension culture, the cells were long-term cultured in a serum medium free of Wnt signaling pathway agonists and FGF signaling inhibitors (NucT2 medium).

Figure 5:
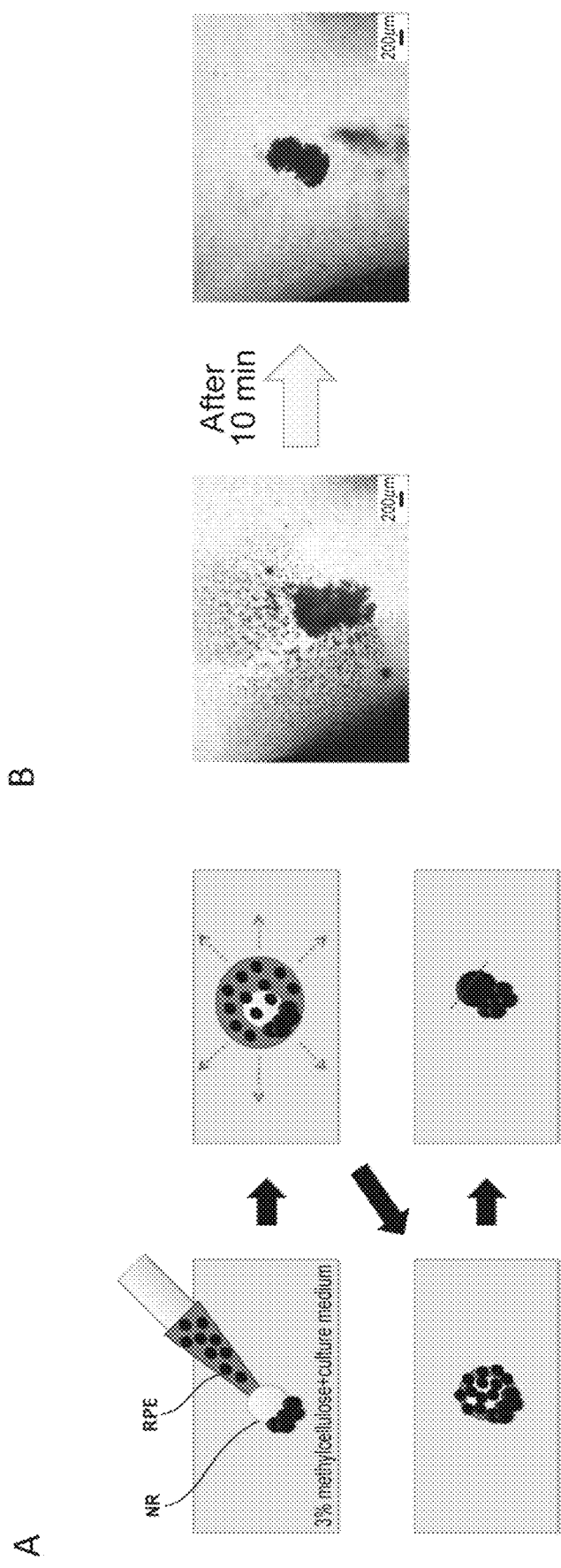
FIG. 5 is diagrams showing the method of adhering NR and RPE cells of Example 3 (A) and microscopic observation results at immediately after and 10 minutes after adhesion (B).
Figure 6:
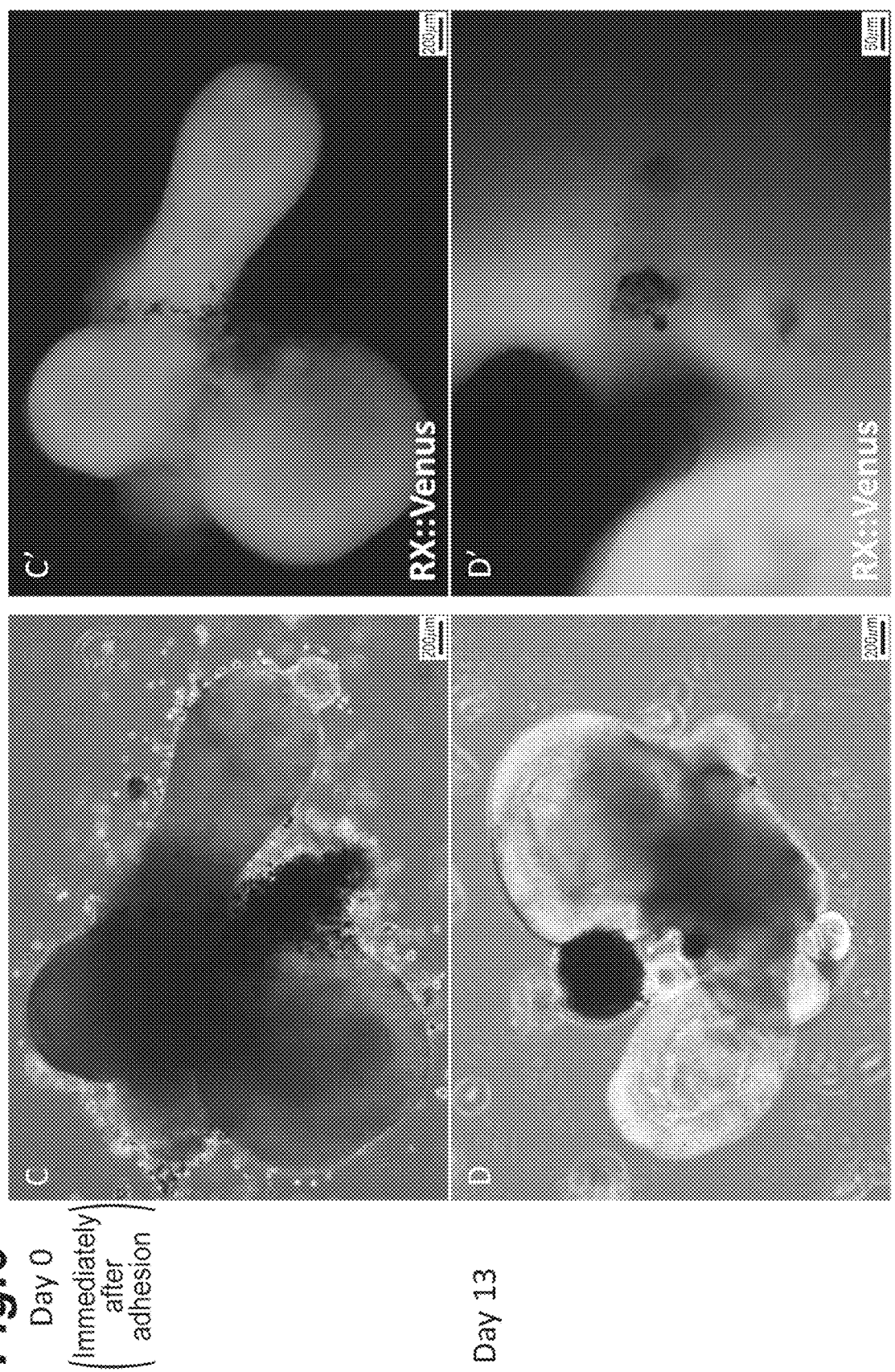
FIG. 6 is diagrams showing the results of observing changes over time at immediately after and day 13 after adhesion of NR and RPE cells in Example 3 with a microscope (C, D) and a fluorescence microscope (C', D').

NR at day 50 to 120 after the start of suspension culture were added to serum medium containing 3% methylcellulose (manufactured by Sigma Aldrich, Inc.) and suspended therein using pipette. In addition, approx. 10 RPE cell aggregates at day 80 to 90 after the start of suspension culture were collected, washed with PBS, and subjected to enzyme treatment with TrypLe™ select (manufactured by Thermo Fisher Scientific, Inc.) for 15 to 60 minutes, and single-cellularized by pipetting. The single-cell dissociated RPE cells were passed through 40 μm Cell Strainer (Falcon), then centrifuged at 800 rpm, and the supernatant was removed. After adding 10 μL of culture medium thereto, 3 μl of the mixture was collected, and ejected towards NR in a serum medium containing 3% methylcellulose (manufactured by Sigma Aldrich, Inc.) (FIGS. 5A, B). When observed with a microscope and a fluorescence microscope within 1 hour, it was confirmed that single-cellularized RPE cells were attached to NR (FIGS. 6C, C'). Thirteen days after adhesion, observation was performed with a microscope and a fluorescence microscope to confirm adhesion on NR (FIGS. 6D, D').

From these results, it was found that adhesion of RPE cells onto NR can be achieved by adding separately prepared RPE cells and NR into a medium containing methylcellulose.

Example 4: Transplantation and Engraftment Confirmation of NR-RPE Cell Sheet

Figure 7:
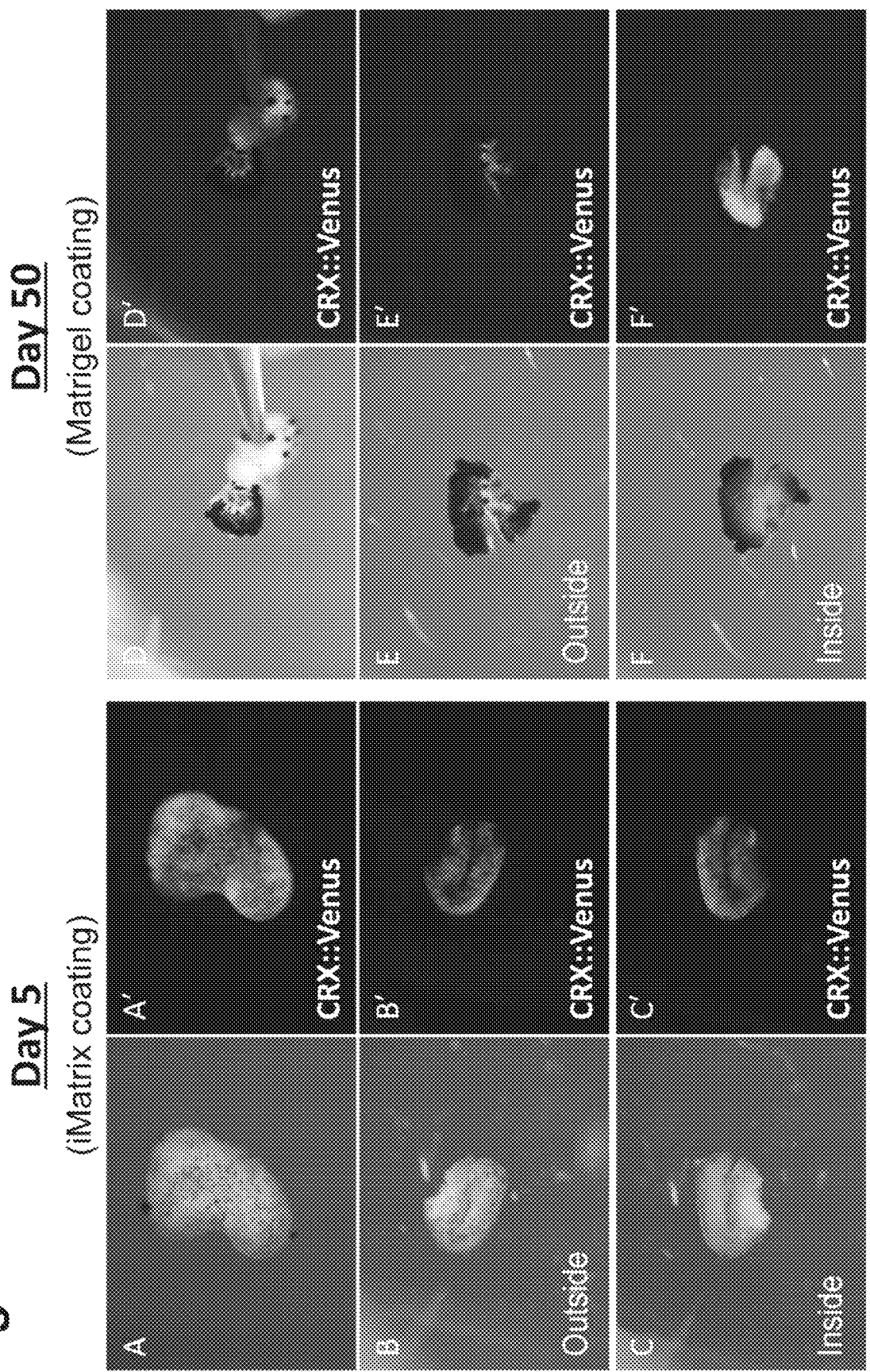
FIG. 7 is diagrams showing the results of culturing the NR-RPE cell sheet produced in Example 4 for 5 days and 50 days after adhesion and observing with a fluorescence microscope (A, B, C, D, E, F), and the results of cutting out the cultured NR-RPE cell sheet and observing with a fluorescence microscope (A', B', C', D', E', F').

The NR-RPE cell sheets produced in Example 2 were conjugated and cultured for 5 days and 50 days in Nuc T2 medium (FIGS. 7A, A', D, D'). From the cultured NR-RPE cell sheets, NR and RPE cells were cut out simultaneously (FIGS. 7B, B', C, C', E, E', F, F'). In the observation with a microscope and a fluorescence microscope, adhesion of RPE cells was observed by observation from the outside, and RPE cells were hardly observed and fluorescence of CRX:: Venus was well confirmed by observation from the inside. Thus, the NR-RPE cell sheet was able to be cut out with polarity.

Figure 8:
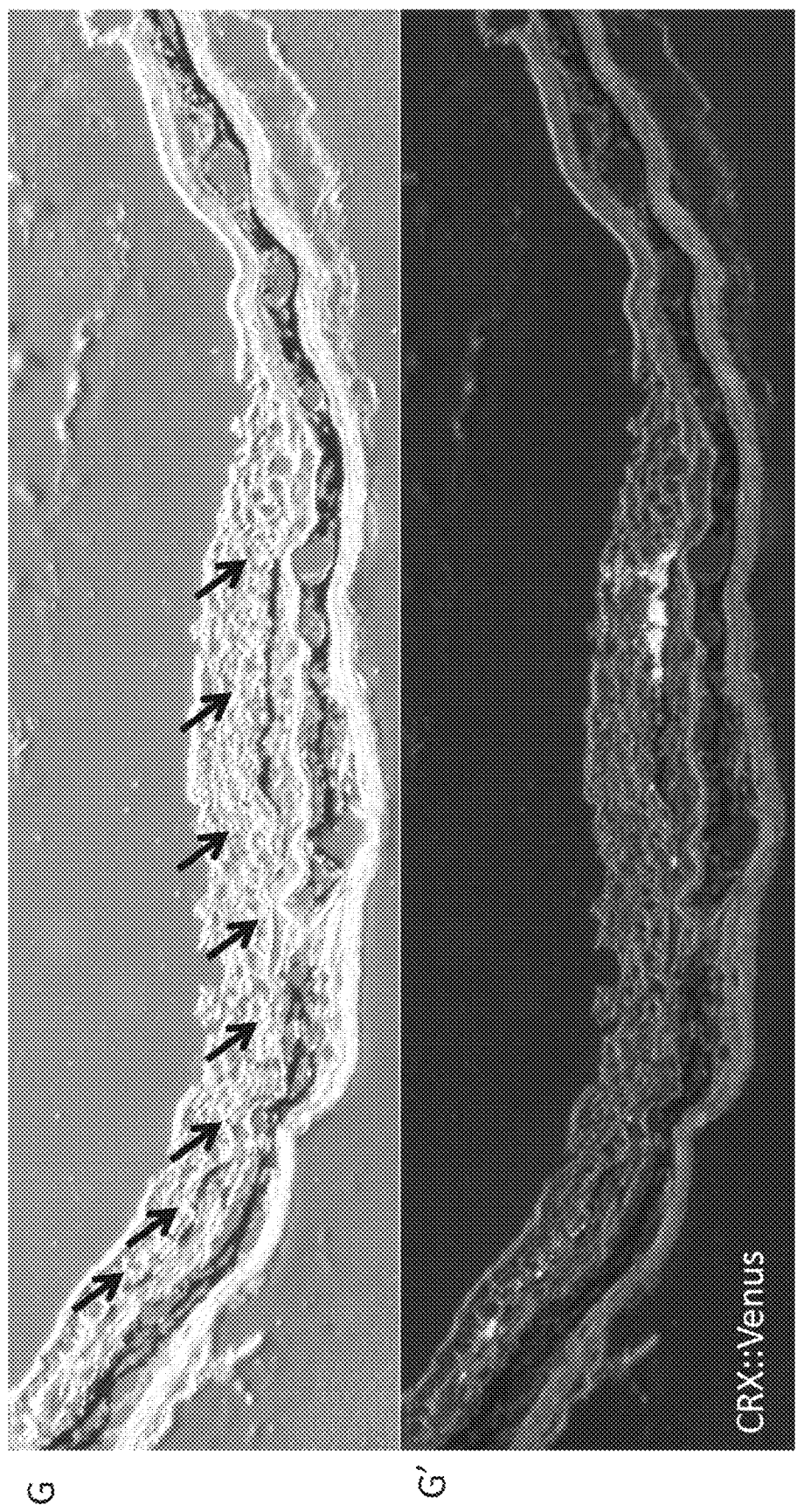
FIG. 8 is diagrams showing the results of observing ocular tissue sections after 5 months or more of transplantation of the NR-RPE cell sheet produced in Example 4 under microscope (G) and under fluorescence microscope (G').

The NR-RPE cell sheets cut out as described above were transplanted with a syringe sub-retinally into a retinal degeneration rat, a photoreceptor cell degeneration model. Five months or more after transplantation, ocular tissues were immobilized with paraformaldehyde (PFA immobilized) and sucrose replacement was performed. Tissue sections were prepared with cryostat (FIGS. 8G, G'). The sections were observed under microscopy and fluorescence microscopy, and it was confirmed that there were an RPE layer on the RPE of Host, and CRX::Venus-positive photoreceptor cell Rosette on the RPE layer (FIGS. 8G, G').

Grafts after transplantation were evaluated by immunostaining using a Rhodopsin antibody (trade name: Anti RetP1 antibody, manufactured by Sigma Aldrich, Inc.). In addition, human cells and RPE cells in the tissue sections were stained with human cytoplasmic marker-specific mouse monoclonal antibody (trade names: Stem 121®, manufactured by Takara Bio Inc.) and anti-RPE 65 antibody (trade names: RPE 65 Antibody, manufactured by Millipore Corporation), respectively, and grafts after transplantation were evaluated.

Figure 9:
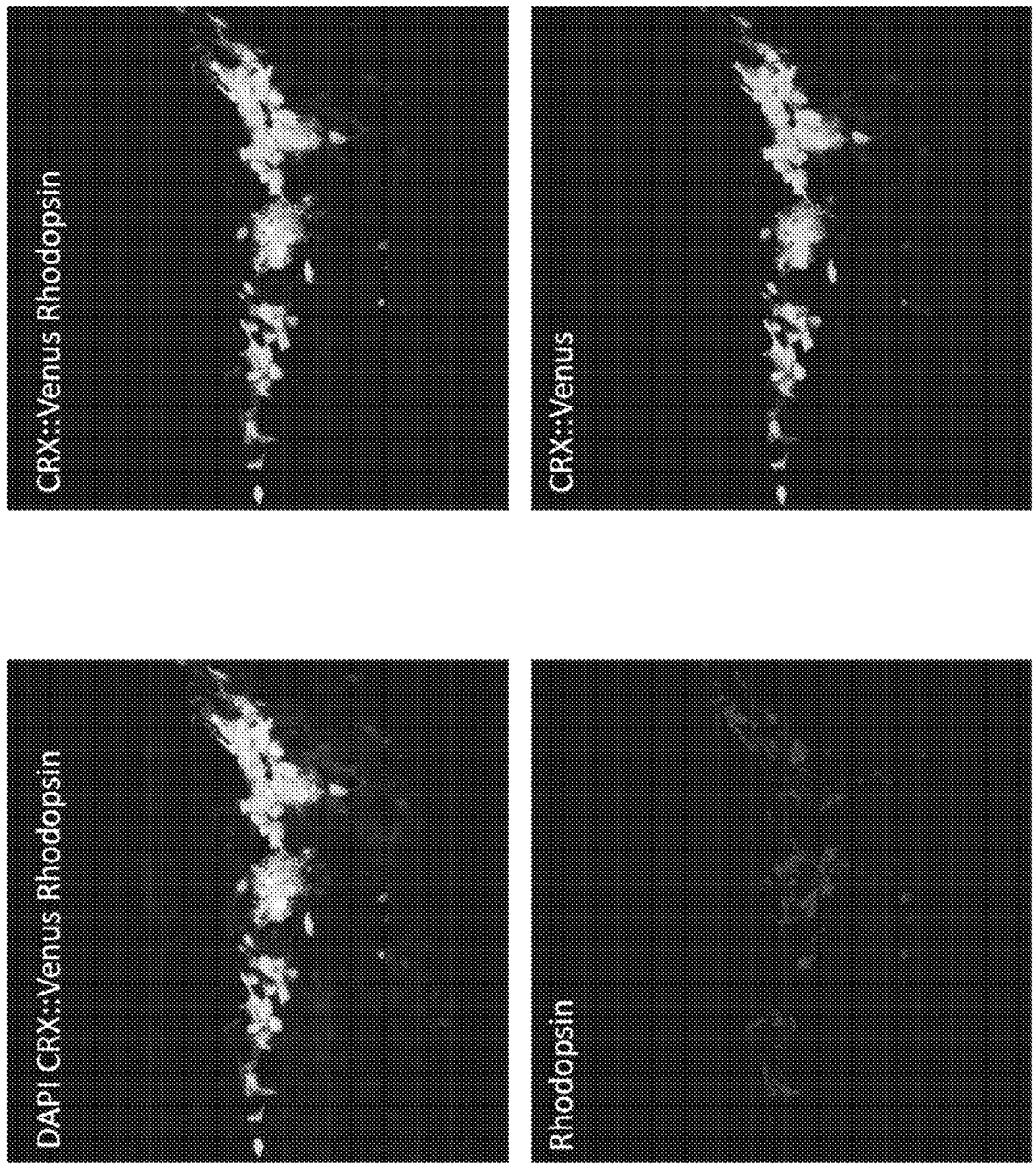
FIG. 9 is a diagram showing the results of immunostained grafts at 5 months or more after transplantation of the NR-RPE cell sheet produced in Example 4 and observed with a confocal fluorescence microscope (H).
Figure 10:
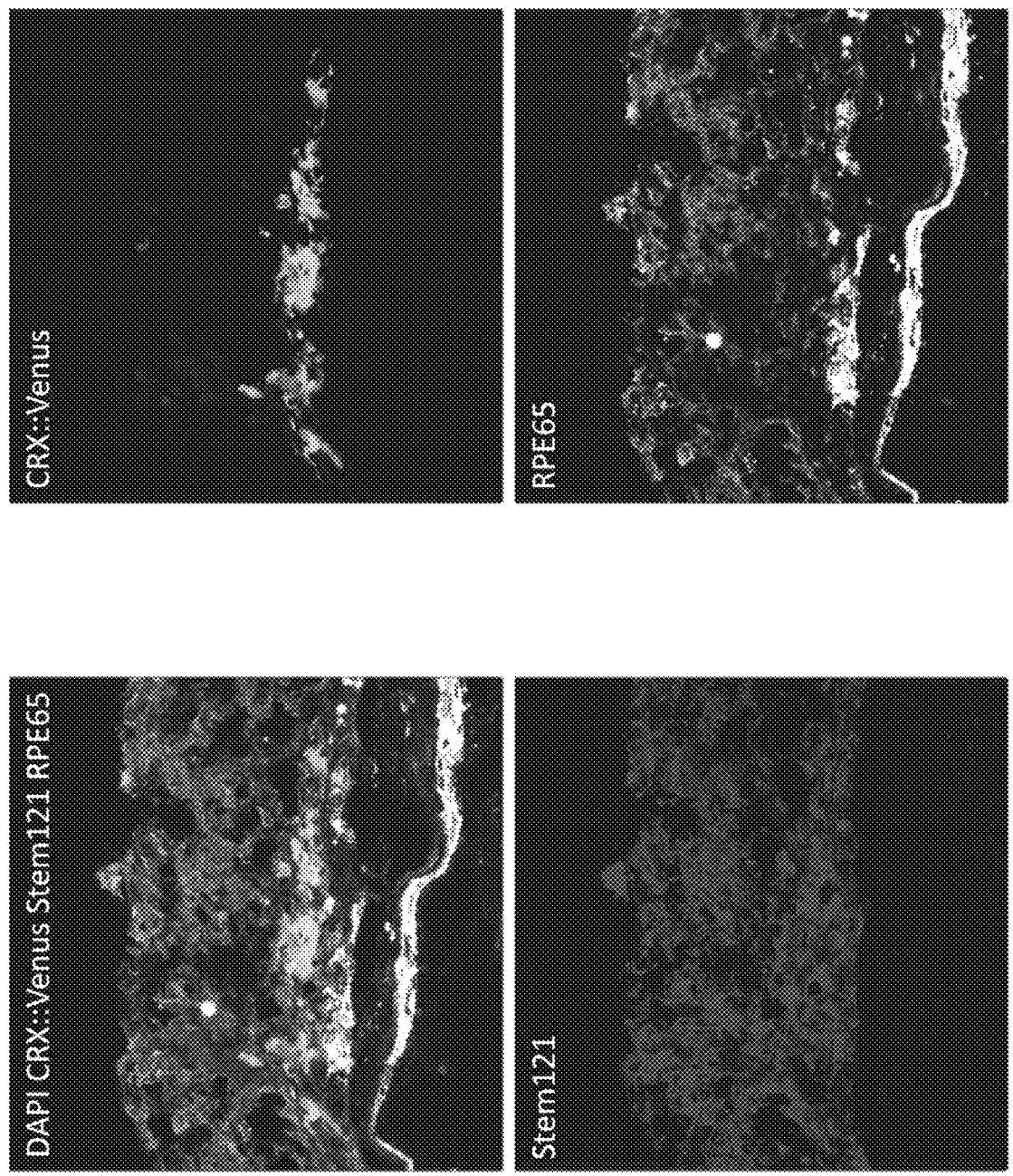
FIG. 10 is a diagram showing the results of immunostained grafts at 5 months or more after transplantation of the NR-RPE cell sheet produced in Example 4 and observed with a confocal fluorescence microscope (I).

The stained tissues were fluorescently observed with a confocal microscope (trade name: TCS SP8, manufactured by Leica Microsystems GmbH). As a result, it was found that photoreceptor cells are Rhodopsin positive and matures without problems even when the photoreceptor cells are transplanted simultaneously with RPE cells (FIG. 9H). Furthermore, from the observation of sections stained with Stem 121® and RPE 65, it was found that the lower RPE 65-positive RPE layers were RPE cells of Host because they were Stem 121® negative, while the upper RPE 65-positive RPE layers were RPE layers derived from Graft since they were Stem 121® positive (FIG. 10I). In addition, CRX:: Venus-positive photoreceptor cell Rosette was observed just above the RPE layers derived from Graft.

From the results, it was shown that, in simultaneous transplantation with a NR-RPE cell sheet, photoreceptor cells become mature, and NR and RPE cells can be transplanted and engrafted simultaneously in a directional manner.

The invention claimed is:

1. A sphere-like cell aggregate comprising:
   a core part consisting of neural retina; and
   a covering part continuously or discontinuously covering at least a portion of a surface of the core part, wherein
   (1) in the neural retina, a neural retinal layer including at least a photoreceptor layer is formed, wherein the photoreceptor layer contains one or more types of cells selected from the group consisting of at least a photoreceptor cell, a photoreceptor progenitor cell, and a retinal progenitor cell, and the cells contained in the photoreceptor layer are continuously present in a tangential direction to the surface of the core part;
   (2) the covering part contains retinal pigment epithelial cells in contact with each other;
   (3) the cell aggregate is free of a crystalline lens, a vitreous, a cornea, and a blood vessel; and
   (4) the retinal pigment epithelial cells in the covering part and the neural retinal layer constituting neural retina in the core part in the sphere-like cell aggregate do not have continuity as an epithelial tissue.

2. The sphere-like cell aggregate according to claim 1, wherein an extracellular matrix is present between the photoreceptor layer in (1) and the retinal pigment epithelial cells covering at least a portion of the photoreceptor layer.

3. The sphere-like cell aggregate according to claim 2, wherein the extracellular matrix includes one or more extracellular matrices selected from the group consisting of hyaluronic acid, laminin, type IV collagen, heparan sulfate proteoglycan, and entactin.

4. The sphere-like cell aggregate according to claim 1, wherein a hydrogel is further present between the photoreceptor cell layer in (1) and the retinal pigment epithelium covering at least a part of the photoreceptor cell layer.

5. A method for producing the sphere-like cell aggregate according to claim 1, comprising:
   preparing a sphere-like cell aggregate containing neural retina (a cell aggregate of neural retina), wherein
   (I) in the cell aggregate of neural retina, the neural retina is present on a surface of the cell aggregate; and
   (II) in the neural retina, a neural retinal layer including at least a photoreceptor layer is formed, wherein in the photoreceptor layer, one or more types of cells selected from the group consisting of a photoreceptor cell, a photoreceptor progenitor cell, and a retinal progenitor cell are present;
   preparing a retinal pigment epithelial cell; and
   contacting the cell aggregate of neural retina with the retinal pigment epithelial cell.

6. The production method according to claim 5, wherein in the cell aggregate of neural retina, a proportion of Chx10 positive cells present in the neural retina is 20% or more.

7. The production method according to claim 5, wherein the contacting step is performed in the presence of an adhesion factor.

8. The production method according to claim 7, wherein the adhesion factor is an extracellular matrix.

9. The production method according to claim 8, wherein the extracellular matrix includes one or more extracellular matrices selected from the group consisting of hyaluronic acid, laminin, type IV collagen, heparan sulfate proteoglycan, and entactin.

10. The production method according to claim 5, wherein at least one of the cell aggregate of neural retina and the retinal pigment epithelial cell is derived from a pluripotent stem cell.

11. The production method according to claim 5, wherein in the step of preparing the retinal pigment epithelial cell, the retinal pigment epithelial cell is prepared as a cell sheet or a cell suspension.

12. The production method according to claim 5, wherein after the contacting step, further culture is performed until the retinal pigment epithelial cell has a polygonal or flagstone-like cell morphology.

13. A reagent for evaluating toxicity or drug efficacy of a test substance, comprising the sphere-like cell aggregate according to claim 1 or a portion of the sphere-like cell aggregate.

14. A method for evaluating toxicity or drug efficacy of a test substance, comprising:
   contacting the sphere-like cell aggregate according to claim 1 or a portion of the sphere-like cell aggregate with the test substance; and
   examining an effect of the test substance on the sphere-like cell aggregate or a cell contained in the sphere-like cell aggregate.

15. A drug for treating a disease based on a disorder of a retinal pigment epithelial cell, a retinal cell or a retinal tissue or a damage of a retinal tissue, comprising the sphere-like cell aggregate according to claim 1 or a portion of the sphere-like cell aggregate.

16. A method for treating a disease based on a disorder of a retinal pigment epithelial cell, a retinal cell or a retinal tissue or a damage of a retinal tissue, comprising transplanting an effective amount of the sphere-like cell aggregate according to claim 1 or a portion of the sphere-like cell aggregate into a subject in need of transplantation.

17. A portion of the sphere-like cell aggregate according to claim 1, wherein the portion is physically cut out from the sphere-like cell aggregate.

18. A portion of the sphere-like cell aggregate according to claim 17, wherein the portion is in the form of a cell sheet containing a retinal pigment epithelial cell and neural retina.

19. A method for producing a portion of a sphere-like cell aggregate, comprising a step of physically cutting out the portion of the sphere-like cell aggregate according to claim 1.

20. The method according to claim 19, wherein the portion of the sphere-like cell aggregate is in the form of a cell sheet containing a retinal pigment epithelial cell and neural retina.

\* \* \* \* \*

UNITED STATES PATENT AND TRADEMARK OFFICE
CERTIFICATE OF CORRECTION

| | |
|---|---|
| PATENT NO. | : 11,684,698 B2 |
| APPLICATION NO. | : 16/643710 |
| DATED | : June 27, 2023 |
| INVENTOR(S) | : Masayo Takahashi et al. |

It is certified that error appears in the above-identified patent and that said Letters Patent is hereby corrected as shown below:

On the Title Page

Item (71) should read: --RIKEN--
Item (73) should read: --RIKEN--

Signed and Sealed this
Fourteenth Day of November, 2023

Katherine Kelly Vidal
*Director of the United States Patent and Trademark Office*